(12) United States Patent
Kaiser et al.

(10) Patent No.: US 9,956,547 B2
(45) Date of Patent: May 1, 2018

(54) PREPARATION OF POLYGLYCEROLS

(71) Applicants: Clariant International Ltd., Muttenz (CH); Universiteit Utrecht Holding B.V., Utrecht (NL)

(72) Inventors: Anton Kaiser, Muehldorf am Inn (DE); Bert Marc Weckhuysen, Houten (NL); Dirk Leinweber, Kelkheim (DE); Fiona Kirby, Frankfurt am Main (DE); Franz Xaver Scherl, Burgkirchen (DE); Hans Joachim Metz, Frankfurt am Main (DE); Pieter Cornelis Antonius Bruijnincx, Utrecht (NL)

(73) Assignees: Clariant International Ltd. (CH); Universiteit Utrecht Holding B.V. (NL)

( * ) Notice: Subject to any disclaimer, the term of this patent is extended or adjusted under 35 U.S.C. 154(b) by 0 days. days.

(21) Appl. No.: 15/117,557

(22) PCT Filed: Feb. 12, 2015

(86) PCT No.: PCT/NL2015/050092
§ 371 (c)(1),
(2) Date: Aug. 9, 2016

(87) PCT Pub. No.: WO2015/122770
PCT Pub. Date: Aug. 20, 2015

(65) Prior Publication Data
US 2016/0354768 A1  Dec. 8, 2016

(30) Foreign Application Priority Data

Feb. 13, 2014 (EP) .................... 14155013
Oct. 31, 2014 (EP) .................... 14191262

(51) Int. Cl.
| | | |
|---|---|---|
| *B01J 27/232* | (2006.01) | |
| *B01J 21/18* | (2006.01) | |
| *B01J 37/03* | (2006.01) | |
| *B01J 37/06* | (2006.01) | |
| *B01J 37/08* | (2006.01) | |
| *B01J 23/02* | (2006.01) | |
| *B01J 35/00* | (2006.01) | |
| *B01J 35/10* | (2006.01) | |
| *B01J 37/02* | (2006.01) | |
| *B01J 35/06* | (2006.01) | |
| *C07C 41/09* | (2006.01) | |
| *C08G 65/34* | (2006.01) | |
| *D06M 15/53* | (2006.01) | |

(52) U.S. Cl.
CPC ............ *B01J 27/232* (2013.01); *B01J 21/18* (2013.01); *B01J 21/185* (2013.01); *B01J 23/02* (2013.01); *B01J 35/002* (2013.01); *B01J 35/006* (2013.01); *B01J 35/1019* (2013.01); *B01J 37/0201* (2013.01); *B01J 37/033* (2013.01); *B01J 37/06* (2013.01); *B01J 37/088* (2013.01); *C07C 41/09* (2013.01); *C08G 65/34* (2013.01); *B01J 35/0013* (2013.01); *B01J 35/06* (2013.01); *D06M 15/53* (2013.01)

(58) Field of Classification Search
CPC . B01J 21/18; B01J 21/185; B01J 23/02; B01J 27/232; B01J 35/002; B01J 35/006; B01J 35/1019; B01J 37/0201; B01J 37/033; B01J 37/06; B01J 37/088; B01J 35/0013; B01J 35/06; C07C 41/09; C08G 65/34
See application file for complete search history.

(56) References Cited

U.S. PATENT DOCUMENTS

| | | | |
|---|---|---|---|
| 3,963,699 A | 6/1976 | Rizzi | |
| 4,517,360 A | 5/1985 | Volpenhein | |
| 4,751,241 A * | 6/1988 | Motoyama | A61K 47/14 514/532 |
| 5,006,648 A | 4/1991 | van der Plank | |
| 5,071,975 A | 12/1991 | van der Plank | |
| 5,079,355 A | 1/1992 | Grechke | |
| 5,585,506 A * | 12/1996 | Harvey | C07C 67/08 554/173 |
| 7,296,691 B2 * | 11/2007 | Koslow | B01D 39/1615 210/500.29 |
| 2006/0240194 A1 | 10/2006 | Lemke | |
| 2008/0306211 A1* | 12/2008 | Lemke | C07C 41/09 525/50 |

FOREIGN PATENT DOCUMENTS

| | | | |
|---|---|---|---|
| EP | 1961726 | * | 2/2007 |
| EP | 1760062 | | 3/2007 |
| WO | 200236534 | | 5/2002 |
| WO | 2010044531 | | 4/2010 |

OTHER PUBLICATIONS

Brunauer, S., et al., "Adsorption of Gases in Multimolecular Layers," Journal of the American Chemical Society 1938, 60, 309.
(Continued)

*Primary Examiner* — Pancham Bakshi
*Assistant Examiner* — Mark R Luderer
(74) *Attorney, Agent, or Firm* — Patterson Intellectual Property Law, PC; Emily A. Shouse; Seth R. Ogden

(57) ABSTRACT

The invention relates to a method for preparing polyglycerol, comprising —providing a catalyst salt on a support, the catalyst salt having catalytic activity with respect to an etherification reaction of a polyol selected from the group of glycerol and oligoglycerols, —contacting the catalyst salt on the support with a fluid phase comprising a polyol selected from the group of glycerol and oligoglycerols, —and subjecting the polyol in the fluid phase to an etherification reaction in the presence of the catalyst salt, thereby forming the polyglycerol.

17 Claims, 18 Drawing Sheets

(56) References Cited

OTHER PUBLICATIONS

Frey et al., "Influence of base strength on the catalytic performance of nano-sized alkaline earth metal oxides supported on carbon nanofibers," Journal of Catalysis 2013, 305, 1-6.
Martin, A., et al., "Oligomerization of glycerol—a critical review," Eur. J. Lipid Sci. Technol. Nov. 17, 2011, 113, 100-117.
Ruppert, A., et al., "Glycerol Etherification over Highly Active CaO-Based Materials: New Mechanistic Aspects and Related Colloidal Particle Formation," Chem. Eur. J. Jan. 29, 2008, 14, 2016-2024.
Sacana et. Al, "Preparation and Properties of Monodisperse Latex Spheres with Controlled Magnetic Moment for Field-Induced Colloidal Crystallization and (Dipolar) Chain Formation," Langmuir 2006, 22, 10209-10216.
European Office Action in corresponding European Patent Application No. 15 707 433.7, dated Jun. 20, 2017, 7 pp.

\* cited by examiner

PREPARATION OF POLYGLYCEROLS

The invention relates to a method for preparing polyglycerol, to a polyglycerol mixture, to a pharmaceutical, cosmetic, food or feed product comprising a polyglycerol mixture and to a method for preparing a pharmaceutical, cosmetic, food or feed product.

Glycerol is an attractive renewable building block for the synthesis of polyglycerols, which have numerous applications in the food, feed, textile, cosmetic and pharmaceutical industries. Polyglycerols are used amongst other as textile lubricants, plastic anti-static agents, defoamers, anti-bloom agents for edible coatings and anti-splattering agents in cooking oil.

Polyglycerols are commonly prepared by mixing glycerol with an alkali metal catalyst, such as sodium or potassium hydroxide, and then heating the mixture to an elevated temperature. This reaction causes the condensation or dehydration of two glycerol molecules' hydroxyl groups. A reaction of two alpha-hydroxyl groups typically results in an ether bond between the glycerol molecules and the release of water to produce a linear polyglycerol. The unreacted hydroxy groups remain available to react with the hydroxy groups of additional glycerol molecules and/or other polymerised molecules. Branched polyglycerols may form by a condensation reaction wherein at least one of the hydroxyl groups is a beta-hydroxyl group.

This method typically produces a mixture of linear, branched, and cyclic polyglycerols.

Cyclic polyglycerols, however, often cause degradation of products into which they are incorporated, detrimentally affecting the colour, taste, performance or odour of the products.

Therefore, there have been continuing efforts to find a method of preparing linear polyglycerols which produce little, if any, cyclic polyglycerols. Cyclic polyglycerols generally have a significantly lower hydrophilic-lipophilic balance (HLB's) than similar linear polyglycerols. As a result, they typically act as emulsion breakers rather than emulsion builders. The presence of cyclic polyglycerols and cyclic polyglycerol esters promotes free polyglycerol in high mono ester products to precipitate out of solution to produce a two phase system. This makes high mono ester products difficult if not impossible to manufacture on a commercial basis. Polyglycerol esters prepared with a low mole ratio of fatty acid to polyglycerol have a tendency not to be homogeneous at reaction temperature. The situation is worse when cyclic polyglycerols are brought into the system.

Many methods for enhancing the colour, odour or taste of polyglycerol mixtures and for reducing the concentration of cyclic polyglycerols in polyglycerol mixtures have been developed. In WO 02/36534, a method is described which makes use of a calcium containing compound, such as calcium hydroxide, whereby the production of cyclic polyglycerols is stated to be greatly reduced compared to a method wherein potassium or sodium hydroxide is used. This effect is not apparent from the Examples of WO 02/36534, though. Further, WO 02/36534 does not specify details on material properties of the calcium containing compound used.

In Chem. Eur. J. 2008, 14, 2016-2024, activity of several alkaline earth metals in a polymerisation reaction of glycerol was studied and compared with a sodium salt ($Na_2CO_3$). Activity was about the same for BaO and SrO, but significantly less for CaO. MgO showed hardly any catalytic activity. It was also found that at the start of the reaction, mainly linear diglycerol was produced, but as the reaction progressed higher degrees of branched diglycerol started to form. Further, effects of different types of CaO materials on the polymerisation of glycerol were studied. It was found that the method of preparing the material had an effect on catalytic properties. After publication of this paper, one of these materials, named 'CaO—C' has been further evaluated by the present inventors, and they found that, at 220° C., it took about 5-6 h before catalytic activity was observed. When solid $Ca(OH)_2$ is tested in glycerol etherification under similar conditions, an induction time of 6-7 h is also observed.

It is an object of the invention to provide a method of preparing a polyglycerol which can be used as an alternative to known methods, in particular to overcome one or more drawbacks of a known method. In particular, it would be advantageous to provide a method with satisfactory activity, a favourable selectivity towards formation of linear polyglycerol molecules, a desirable colour or an improved product property for a specific application, such as improved emulsifying properties.

It is a further object to provide a novel polyglycerol mixture, in particular a novel polyglycerol mixture suitable for use in a pharmaceutical, cosmetic, food, feed or textile.

It has now been found that an object of the invention is met by contacting glycerol or an oligoglycerol with a catalyst salt provided in a specific form.

Accordingly, the invention relates to a method for preparing polyglycerol, comprising providing a catalyst salt on a support, the catalyst salt having catalytic activity with respect to an etherification reaction of a polyol selected from the group of glycerol and oligoglycerols, contacting the catalyst salt on the support with a fluid phase comprising a polyol selected from the group of glycerol and oligoglycerols, and subjecting the polyol in the fluid phase to an etherification reaction in the presence of the catalyst salt, thereby forming the polyglycerol.

Further, the invention relates to a polyglycerol mixture, in particular a mixture obtainable by a method according to the invention.

Typically a polyglycerol mixture according to the invention has a hydroxyl value in the range of 807-1352 mg KOH/g, preferably in the range of 846-1072 mg KOH/g, as determined by DIN 53240; and a Gardner colour number, as determined by DIN ISO 4630, of less than 6, preferably of 2 or less, in particular of 1.5 or less.

The invention further relates to a method for preparing a polyglycerol derivative, comprising reacting the polyglycerol obtained in a method according to the invention or a polyglycerol mixture according to the invention with a substance having reactivity with a hydroxyl group of the polyglycerol.

The invention further relates to a polyglycerol derivative obtainable by a method for preparing a polyglycerol derivative according to the invention.

The invention further relates to a product comprising a polyglycerol or polyglycerol derivative according to the invention or obtained by a method according to the invention and one or more other components.

In particular, the invention further relates to a pharmaceutical product, a cosmetic product, a textile product, a food product or a feed product, comprising (i) a polyglycerol mixture obtained in a method according to the invention or, a polyglycerol mixture according to the invention or a polyglycerol derivative obtainable in a method for preparing a polyglycerol derivative according to the invention (ii) and one or more other ingredients for any of said products.

The invention further relates to the preparation of a pharmaceutical product, a cosmetic product, a textile product, a food product or a feed product according to the invention, in which product a polyglycerol mixture or polyglycerol derivative made by a method according to the invention is provided.

The invention further relates to a method for preparing a pharmaceutical product, a cosmetic product, a textile product, a food product or a feed product, comprising combining a polyglycerol mixture obtained in a method according to the invention, a polyglycerol mixture according to the invention, or a polyglycerol derivative obtainable in a method according to the invention with one or more other ingredients for any of said products.

The invention further relates to a catalyst salt on a support, the catalyst salt having catalytic activity with respect to an etherification reaction of a polyol selected from the group of glycerol and oligoglycerols. In particular, good results have been achieved with a calcium oxide being either on a carbon nanofiber or on activated carbon.

FIG. 1(a) shows a TEM images of the catalyst of Example 9 (2.5 wt. % CaO on CNF); FIG. 1(b) shows a TEM image of the catalyst of Example 8 (4.8 wt. % CaO on CNF); FIG. 1(c) shows a TEM image of the catalyst of Example 1 (14 wt. % CaO on CNF) in bright field.

FIG. 2 shows the XRD patterns of the catalysts according to Examples 7 (10 wt. % CaO on CNF), 10 (10 wt. % $Ca(OH)_2$ on CNF) and 11 (10 wt. % $CaCO_3$ on CNF).

FIG. 3 (a) shows the activity of the catalysts of Example 1 (line with triangles), Example 2 (line with circles), Example 3 (line with crosses), Example 4 (line with squares) and Example 5 (line with diamonds). FIG. 3 (b) shows the activity of the catalysts of Example 1 (line with filled triangles) and Example 13 (line with filled squares). FIG. 3 (c) shows the activity of the catalysts of Examples 15 (line with filled squares) and 14 (line with filled diamonds).

FIG. 4 shows a bar graph of the polyglycerol product distribution obtained at a reaction time of about 24 h for the catalysts of Examples 1-3, 5 and 6. The products that were measured include glycerol (fine cross hatch), diglycerol (thick diagonal lines), triglycerol (coarse cross hatch), tetraglycerol (vertical lines) and higher oligomers (dots).

FIGS. 5 and 6 show bar graphs of the polyglycerol product distribution obtained at about 30% conversion using catalyst Examples 1, 2 and Example 6 and about 50% conversion using catalysts according to Examples 1-3, 5 and 6, respectively. The products that were measured include glycerol (fine cross hatch), diglycerol (thick diagonal lines), triglycerol (coarse cross hatch), tetraglycerol (vertical lines) and higher oligomers (dots).

FIGS. 7-12 show the selectivity of the catalysts of Examples 1-3, 5 and 6, as well as the catalyst of Example 1 using a reaction temperature of 200° C., respectively, for converting glycerol (line with squares) to cyclic dimers (line with triangles), diglycerol (line with crosses), cyclic trimers (line with crosses having a vertical line), triglycerol (line with circle), tetraglycerol (line with vertical lines) and higher oligomers (line with diamonds).

FIG. 13 shows the glycerol conversion for the catalysts of Example 7 (line with filled diamonds), Example 8 (line with filled circles), Example 9 (lines with filled triangles) and 35.7 mmol of the bulk catalyst of Example 12 (line with stars) as a function of time.

FIGS. 14 and 15 show a bar graph of the polyglycerol product compositions obtained for the CaO on CNF catalysts of different weight loadings (Examples 7-9, respectively) at 30% conversion and after 24 h, respectively. The different polyglycerol products obtained are indicated in FIGS. 14 and 15 as follows: glycerol (fine cross hatch), dimers (thick diagonal), trimers (coarse cross), tetramers (vertical lines) and higher oligomers (dots).

Figure 18:
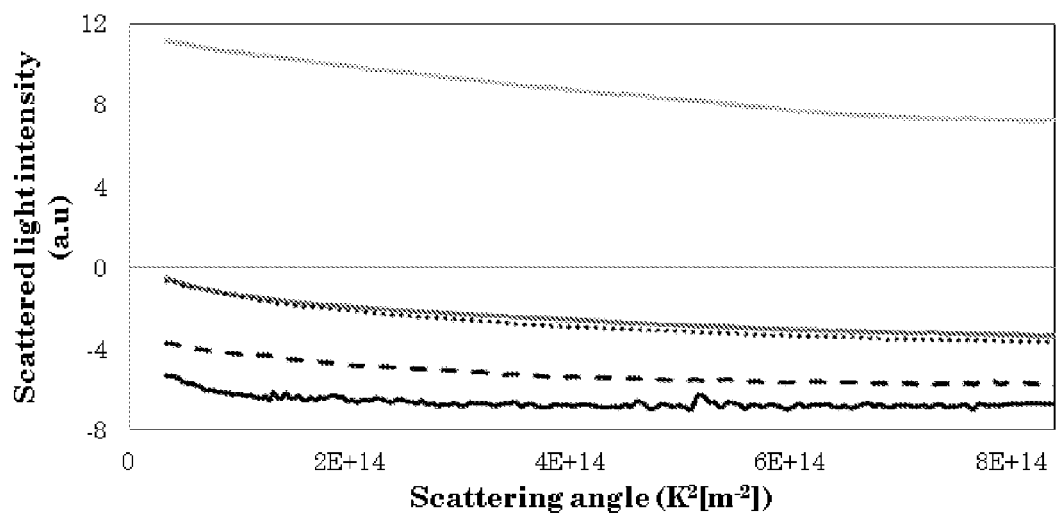

FIG. 18 shows the results of the SLS measurements in a graph plotting the scattered light intensity (a.u.) vs. the scattering angle ($K^2[m^{-2}]$) for the catalysts of Example 1 (black dotted line) and Example 8 (black dashed line), their equivalent Ca molar amounts of 5 mmol and 1.7 mmol of the catalyst of Example 3 (light grey [top curve] and dark grey [close to dotted line], respectively) and glycerol (black).

Figure 19:
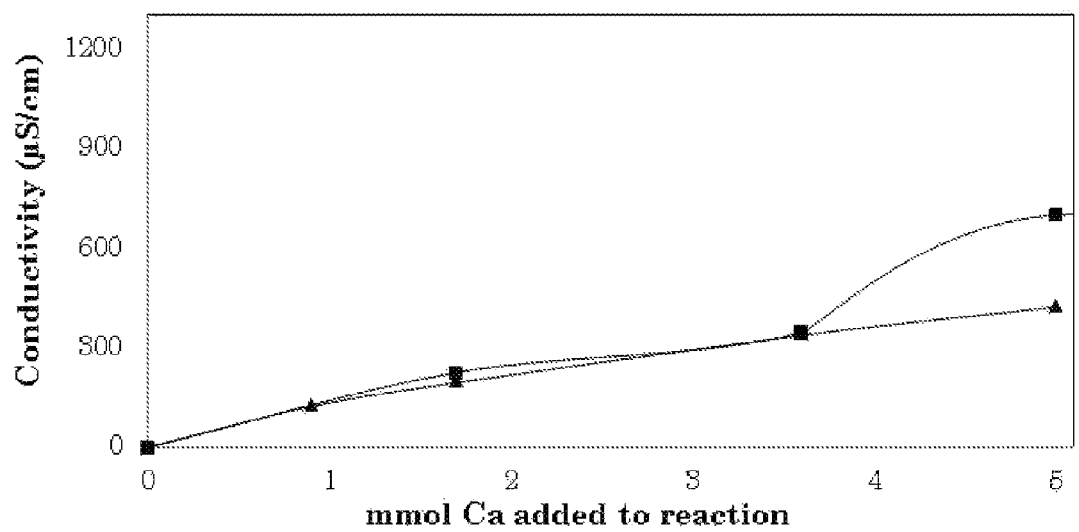

FIG. 19 shows the conductivity (μS/cm) of the polyglycerol product mixtures obtained vs mmol Ca added to the reaction using 2 wt. % of the catalysts of Examples 1, 7-9 (line with filled squares); and 1.7 mmol and 5 mmol of the catalyst of Example 3 (line with filled triangles) after 24 h reaction time.

Figure 20:
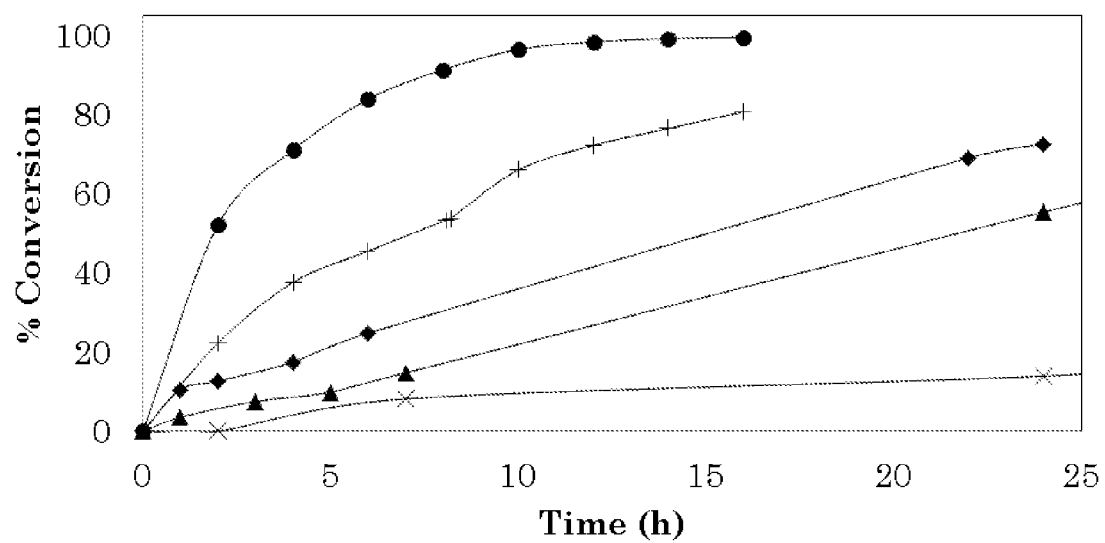

FIG. 20 shows the effect of reaction temperature on glycerol conversion in a graph plotting % glycerol conversion vs time (h), with the catalyst of Example 7 (10 wt. % CaO on CNF) at reaction temperatures of 180° C. (line with x's), 200° C. (line with filled triangles), 220° C. (line with filled diamonds), 240° C. (line with +'s) and 260° C. (line with filled circles).

The inventors found that a considerable delay in the start of the reaction, observed with an unsupported catalyst salt, such as an alkaline earth metal oxide described in Chem. Eur. J. 2008, 14, 2016-2024 (CaO), did not occur when a catalyst salt on a support was used. It was further found that the method of the invention was effective in forming linear polyglycerol molecules of various lengths in a shorter period of time.

Regarding colour, the invention is in particular advantageous in that is allows the preparation of a polyglycerol mixture, which is essentially colourless or has a light colour. Usually the Gardner colour number is less than 6. Preferably, the Gardner colour number is 3 or less, more preferably 2 or less, in particular of 1.5 or less, more in particular 1.0 or less. The Gardner colour number is as defined by DIN ISO standard 4630.

Polymers are molecules at least conceptually composed of two or more smaller molecules (i.e. monomer molecules), such as glycerol. Oligomers are a species of polymers, namely relatively small polymers, typically at least conceptually composed of 2-40 monomer units, such as 2-40 glycerol units.

The term 'polyglycerol' is used herein for linear, branched and cyclic molecules at least conceptually composed of two or more glycerol molecules. When used in relation to a method for preparing glycerol the term polyglycerol is in particular used for the reaction product. The term 'oligoglycerol' is used herein specifically for a starting material at least conceptually composed of two or more glycerol molecules. As will be understood by the skilled person, a polyglycerol obtained by a method of the invention or present in a product according to the invention can be an oligomer of glycerol; it will typically be composed (i.e. at least conceptually) of at least one additional glycerol compared to the oligoglycerol from which it was made from.

For the purpose of clarity and a concise description, features are described herein as part of the same or separate embodiments, however, it will be appreciated that the scope of the invention may include embodiments having combinations of all or some of the features described.

The catalyst salt is selected from any catalyst salt having catalytic activity with respect to an etherification reaction of a polyol selected from the group of glycerol and oligoglycerols. Preferably, the catalyst salt is an alkaline salt (i.e. a salt providing alkaline pH in a protic medium), such as a hydroxide, a carbonate or an oxide. Usually, the catalyst salt is a metal salt. Preferably, the catalyst salt is selected from the group of alkaline earth metal salts and alkali metal salts, more preferably from the group of alkaline earth metal salts. Particularly preferred is an alkaline earth metal salt selected from the group of calcium oxide, magnesium oxide, barium oxide, strontium oxide, calcium hydroxide, calcium carbonate, magnesium hydroxide, barium hydroxide and strontium hydroxide, and even more preferably from the group of calcium oxide, magnesium oxide, calcium hydroxide, calcium carbonate and magnesium hydroxide. In particular, good results have been achieved with an alkaline earth metal oxide, such as calcium oxide.

Previous studies, as described in Eur. J. Lipid Sci. Technol. 2011, 113, 100-117, with bulk CaO, $CaCO_3$ and $Ca(OH)_2$ have shown that even though CaO is a stronger base than $Ca(OH)_2$ and $CaCO_3$, $Ca(OH)_2$ is more active than CaO and $CaCO_3$ in the etherification of glycerol, due to the higher solubility of $Ca(OH)_2$ in glycerol and its polymeric products at elevated temperatures. Surprisingly it has been found that by distributing CaO on a CNF support both the availability of CaO and the catalytic activity is increased. It is believed that this indicates that the activity of catalysts in glycerol etherification is dependent on the availability of active phase and the base strength of the catalyst used.

The support is usually a material upon which the catalyst salt has been deposited. Suitable materials for the support are those materials, which are essentially inert in a fluid phase, (i.e. will neither chemically nor physically decompose, e.g. by dissolving or melting).

Usually a material is chosen for the support that also acts as a release material for the catalyst salt from the support to the fluid phase. Preferably, the catalyst salt is released from the support into the fluid phase as colloidal particles when contacting the catalyst salt on the support with the fluid phase, optionally when heating the fluid phase whilst the catalyst salt on the support is in contact with the fluid phase, or by adding the catalyst salt on support to a heated fluid phase. The temperature to which the fluid phase can be heated can be any temperature suitable for carrying out an etherification reaction. Surprisingly it was found that the colloidal particles of the released catalyst salt have a higher activity than equimolar amounts of known bulk CaO and NaOH catalysts in the etherification of glycerol. This is believed to be attributed to the smaller size of the colloids originating from the catalyst salt on the support compared to colloids produced from bulk catalyst salts. The colloidal particles preferably have a diameter, as determined by dynamic light scattering (DLS), of 400 nm or less, preferably 300 nm or less, in particular of 20-250 nm, more in particular of 50-200 nm. These diameters are as determined by a DLS measurement using the following conditions: prepare 50 wt. % samples of polyglycerol in $H_2O$. The samples were filtered with Milliporous FP 0.8 μm filters. Measure DLS of the filtered samples on a Malvern Zetasizer Nano.

The colloid particles generally have a high polydispersity. The size distribution may be polymodal, e.g. having a peak at about 60 nm to about 75 nm and a peak at about 150 nm to about 180 nm.

In particular, a catalyst salt on a support is preferred, wherein at least the majority, i.e. more than 50 wt. %, preferably at least 90 wt. %, of the catalyst salt (before contacting it with the fluid phase) is present at the surface of the support in the form of nanoparticles, generally having a size of 100 nm or less, preferably of 50 nm or less, more preferably having a size of less than 30 nm, and in particular a size of 10 nm or less. Usually, the size is at least 1 nm, as determinably by transmission electron microscopy (TEM). Preferably, essentially all of the catalyst salt is present as nanoparticles deposited on the support (prior to contacting it with the fluid phase). It has been found that in particular at a relatively low catalyst salt concentration, typically of less than 15 wt. %, in particular of less than 10 wt. %, more in particular 5 wt. % or less that a large fraction (i.e. more than 50 wt. %) or essentially all (i.e. more than 90 wt. %, in particular more than 95 wt. %) of the catalyst salt is provided as nanoparticles. Regarding a lower limit for the catalyst salt concentration, the catalyst concentration usually is 1 wt. % or more, in particular 2 wt. % or more, based on the total weight of the catalyst salt and support.

Alternatively, or in addition catalyst salt may be present in the form of a film or sheet on the support.

Such an embodiment of the invention, wherein the catalyst salt is released as colloidal particles in the fluid phase, wherein the etherification reaction proceeds, is a facile way to introduce colloidal metal salt catalyst in the reaction phase. Further, this approach has been found to be particularly advantageous in that the induction time, i.e. the time between bringing the fluid phase to a temperature at which the etherification reaction proceeds and the moment at which a significant catalyst activity is noticeable, is relatively short, typically less than one hour. It is envisaged that, at least in some embodiments, the induction time is 0, i.e. the catalyst has significant activity upon reaching the temperature at which the etherification proceeds. In contrast, in a method wherein metal salt particles are dispersed without the aid of the support (e.g. the CaO—C material used in Chem. Eur. J. 2008, 14, 2016-2024 and WO 02/36534), the induction time is considerably longer, for instance more than four hours at 220° C. Moreover, it was found that a catalyst salt provided in accordance with the invention is more active than bulk catalyst salt (such as the CaO—C from Chem. Eur. J. 2008, 14, 2016-2024). Moreover, the catalyst activity is higher, i.e. high conversion is reached within less time, in particular for a support comprising more than 5 wt. % of a catalyst salt, on the total weight of the catalyst salt and support. This is believed to be the result of a contribution from a heterogeneous reaction pathway, due to the presence of colloidal particles of the catalyst salt. Whereas at lower amounts of catalyst salt the reaction is believed to be dominated by a homogeneous reaction pathway which is limited by solubility of the catalyst salt.

Further advantages of this embodiment of the invention are that it is not only suitable for the production of higher oligomers of glycerol (i.e. polyglycerols molecules which consist of two or more glycerol unit per molecule), but minimises the colouration of the polyglycerol mixture product and substantially avoids the formation of acrolein (i.e. usually 0.01 wt. % or less, preferably 0.001 wt. % or less).

With respect to the support material, good results have been achieved with a carbon material, in particular with carbon nanofibers (CNFs) and activated carbon. Further preferred carbon materials include, single wall carbon nanotubes or multi-wall carbon nanotubes (SWCTs or MWCNTs), graphitic carbon and carbon black. The carbon may be a non-activated carbon or an activated carbon. An example of an activated carbon is Norit® SX Ultra Cat, which is an acid-washed, steam-activated carbon powder from Cabot Norit Americas Inc). Carbon material is particularly suitable for use as support since it is inert, in particular if non-activated carbon is used, and allows advantageous release of the catalyst salt.

Nanofibers, nanotubes and other supports with an elongate structure are in particular preferred support materials, for their advantageous surface area to volume ratio.

CNFs (of non-activated carbon) are preferred not only for their advantageous surface area and inertness, but also because they can be made with high purity.

Activated carbon is also a preferred support material because not only of its high surface area, inertness and the fact that it can be made with high purity, but also because such materials are more favourable economically to use in industrial-scale applications due to their relatively low cost.

Usually, the support has a BET surface area, as determinable by $N_2$-physisorption, of 1200 m$^2$/g or less, in particular 50-500 m$^2$/g, more in particular 100-200 m$^2$/g.

The BET surface area, as determinable by $N_2$-physisorption, of the support including the catalyst salt is typically 1100 m$^2$/g or less, preferably 30-450 m$^2$/g, and more preferably 50-150 m$^2$/g.

The BET surface is determinable by the method as described by (S. Brunauer, P. H. Emmett and E. Teller, Journal of the American Chemical Society 1938, 60, 309). The BET surface area is defined herein as the value that can be measured by determining the amount of nitrogen adsorbed at 77 K and $P/P_0$ of approximately 0.05 to 0.3, where P is partial vapour pressure of nitrogen in equilibrium with the surface at 77 K and $P_0$ is the saturation pressure of nitrogen, and assuming a nitrogen cross sectional area of 16.2 Å$^2$, after degassing the sample at 180° C. on a Micromeritics Tristar 3000.

Usually, the total pore volume of the support is 1.5 mL/g or less, in particular of 0.3-1.0 mL/g, more in particular of 0.4-0.6 mL/g.

The total pore volume of the support including the catalyst salt is typically 1.1 mL/g or less, in particular 0.25-0.9 mL/g, more in particular 0.3-0.5 mL/g.

The total pore volume, as used herein, is the value measured by determining the volume of liquid nitrogen adsorbed at $P/P_0$ of approximately 1 using a Micromeritics Tristar 3000.

The amount of catalyst salt on the support can in principle be chosen within wide limits. The support usually comprises at least 1 wt. % catalyst salt, preferably at least 2 wt. %, in particular at least 4 wt. %, based on the total weight of the catalyst salt and support (at least before contacting). For advantageous release behaviour into the fluid phase wherein the etherification typically takes place, it is preferred that the catalyst salt is distributed on the surface of the support as discrete nanoparticles. The distributed nanoparticles preferably have a size as described above. Usually, the amount of catalyst salt on the support is 15 wt. % or less, preferably 10 wt. % or less; and, usually 2 wt. % or more, preferably 4 wt. % or more, more preferably 5 wt. % or more, based on the total weight of the catalyst salt and support.

The catalyst salt on the support can be prepared in a manner known per se. In particular, an incipient wetness impregnation (IWI) method is suitable. For example, the preparation of the catalyst salt may be based on Frey et al., ChemCatChem 2013, 5, 594-600 or Frey et al., Journal of Catalysis 2013, 305, 1-6. In IWI, a support is impregnated with an impregnation salt solution, which salt at least provides the cation (typically a metal ion) for the catalyst salt. In principle, the salt may be selected from any salt that dissolves in the impregnation liquid, which may be an aqueous liquid or an organic liquid. The salt may be a salt of an organic acid, such as formic acid or acetate. In an advantageous embodiment, the salt is an inorganic salt, such as a halogen salt, in particular a chloride salt; a nitrate salt; or a sulphate salt. Good results have been achieved with a nitrate salt.

After impregnation, the impregnated support is usually dried. The drying may be carried out in a manner known per se.

If desired, the impregnated support is subjected to heat treatment, whereby the salt (other than an oxide) on the support is converted into an oxide thereby forming the catalyst salt (oxide) on the support, in a manner known per se, for instance by heating at a temperature of about 800° C.

In a method for preparing polyglycerol according to the invention, the catalyst salt is usually provided in an amount to provide a molar ratio of the catalytic salt to polyol (at the beginning of the reaction) of 0.0001 or more, in particular 0.0002 or more, more in particular 0.0004 or more. For a high activity, it is preferred to use a relatively high ratio, such as a ratio of 0.0005 or more, in particular 0.001 or more. Usually the molar ratio of the catalytic salt to the polyol (at the beginning of the reaction) is less than 0.01, preferably 0.005 or less, more preferably 0.004 or less in particular 0.003 or less. A relatively low ratio is advantageous, in that the presence of the metal catalyst salt in the obtained product is usually not demanded or desired. Thus, by using a low ratio the need for a removal step may be omitted, or at least be less intense, since the polyglycerol mixture obtainable by a method of the invention typically comprises 0-2000 ppm by weight of calcium, preferably 0-2000 ppm by weight of alkaline earth metals and alkali metals, more preferably 0-2000 ppm by weight of metals. Apart from good results with respect to activity and selectivity, the use of a calcium oxide, carbonate or hydroxide or a magnesium oxide or hydroxide as the catalyst salt is also considered to be advantageous, as in many applications the presence of calcium or magnesium is less seen as undesired than, e.g. sodium.

The etherification reaction is typically carried out in a fluid phase essentially consisting of a catalyst salt and a polyol. Usually, the total weight of the catalyst salt plus the polyol (i.e. the initial reagents glycerol/oligoglycerol and the formed polyglycerol) in the fluid phase during etherification is at least 90 wt. %, preferably at least 95 wt. %, more preferably at least 99 wt. %, and in particular at least 99.8 wt. %, based on total weight of the fluid phase. As will be clear to the skilled person, the support if still present in the reactor wherein the reaction is carried out) is typically solid, and thus does not form part of the fluid phase.

During etherification, water is formed. The water is preferably removed during the etherification, in order to suppress the reverse reaction (hydrolysis). If present, the amount of water during etherification is usually less than 0.5 wt. % based on total weight of the fluid phase in which the reaction takes place, preferably 0.2 wt. % or less.

Removal of water (thereby maintaining a low water concentration) can be accomplished in a manner known per se, such as by performing the reaction at a sub-atmospheric pressure, in particular at pressure of less than 0.5 bar (i.e. less than 50 kPa), more in particular of 10-300 mbar (i.e. 1 kPa to 30 kPa).

In an advantageous embodiment, nitrogen gas is sparged through the fluid phase in order to remove water.

It is also possible to add a solvent that promotes water removal, typically a hydrophobic organic solvent, such as toluene. However, it is preferred to carry out the method without such a solvent, unless the presence thereof is desired in the application for which the polyglycerol mixture is intended.

When the catalyst salt has been released from the support, the support may be separated from the reaction medium, prior to, during, or after the etherification reaction has completed or is stopped.

The etherification reaction is usually initiated by increasing the temperature to a temperature at which the reaction proceeds. In general, a temperature of at least about 180° C. is sufficient. For increased reaction rate, a temperature of at least 200° C. is preferred. The temperature is usually 260° C. or less, in order to keep undesired side-reactions such as cyclisation at an advantageously low level. However, in particular at a temperature of about 260° C. or more acrolein and condensation products can be observed, which darken the polyglycerol mixture product. Preferably, the temperature is 240° C. or less, in particular 225° C. or less, more in particular about 220° C. or less.

In principle the obtained polyglycerol may have any length, in particular a length in the range of 2-30 glycerol units. Preferably, at least 10 wt. % of the polyglycerol molecules is formed of at least three glycerol units.

The invention is in particular suitable to prepare a polyglycerol mixture (a mixture of polyglycerols, which may further comprise monomeric glycerol). In particular, the invention is suitable to obtain polyglycerol formed of 2-30 glycerol units, more in particular 2-20 glycerol units.

The hydroxyl value (HV) of the polyglycerol mixture provides an indication for the average size of the polyglycerols (by measuring of the content of free hydroxyl groups in the polyglycerol mixture), which is usually 1352 mg KOH/g (corresponding to the HV of diglycerol) or less, preferably 1169 mg KOH/g (corresponding to the HV of triglycerol) or less, more preferably 1072 mg KOH/g (corresponding to the HV of tetraglycerol) or less, in particular 1012 mg KOH/g (corresponding to the HV of pentaglycerol) or less. Preferably, the reaction is proceeded until a polyglycerol mixture is obtained with a HV of 807 mg KOH/g or more (corresponding to the HV of 27-glycerol), in particular a HV of 824 mg KOH/g or more (corresponding to the HV of 20-glycerol), more in particular a HV of 846 mg KOH/g (corresponding to the HV of pentadeca-glycerol) or more.

The hydroxyl value (HV) in mg KOH/g, as used herein, is the value as determinable by DIN 53240, wherein a polyglycerol sample is first acetylated with acetic anhydride in a pyridine solvent, then water is added to hydrolyze the remaining acetic anhydride to produce acetic acid, and the resulting acetic acid is titrated with a titrant up to the endpoint on a Kyoto Electronics Manufacturing titration system or a Metrohm 904 Titrando.

The polyglycerol mixture (obtainable) according to the invention usually consists of at least 85 wt. %, in particular at least 90 wt. % of polyglycerols.

Usually, the polyglycerol mixture (obtainable) according to the invention comprises more than 30 wt. % linear polyglycerols, based on total polyglycerols, in particular more than 50 wt. %, preferably at least 70 wt. %, more preferably at least 85 wt. %, even more preferably at least 95 wt. %. In a particularly preferred embodiment the polyglycerol mixture (obtainable) according to the invention comprises at least 98 wt. % linear polyglycerols, based on total weight of polyglycerols.

The cyclic polyglycerol content usually is less than 8 wt. %, based on the total weight of polyglycerols, preferably less than 5 wt. %, more preferably less than 2 wt. %.

In particular, it has been found that a method according to the invention allows the preparation of a polyglycerol mixture, with a relatively low number of unsaturated carbon-carbon bonds compared to a commercial reference polyglycerol mixture having a similar average molecular mass. For instance, the invention allows the production of a polyglycerol mixture with an average number of glycerol units of 7-11 having a iodine value of 8 or less, whereas a commercial reference product (made by NaOH catalysis) having an average number of glycerol units of 7-10 had a iodine value of 16.6.

Thus, the iodine value of a polyglycerol mixture (obtainable) according to the invention usually is in the range of 0-10, in particular in the range of 0.5-5. Preferably the iodine value is 3 or less, more preferably 2 or less.

The polyglycerol mixture obtainable in a method according to the invention typically comprises 0-2000 ppm by weight of calcium, and in particular of 10-1000 ppm by weight of calcium.

The content of alkaline earth metals and alkali metals in a polyglycerol mixture obtainable in a method according to the invention preferably is 0-2000 ppm by weight of, in particular 10-1500 ppm by weight, more in particular 100-1000 ppm by weight.

The total content of metals in a polyglycerol mixture obtainable in a method according to the invention is preferably 0-2000 ppm by weight of, in particular 10-1500 ppm by weight, more in particular 100-1000 ppm by weight.

Usually, the polyglycerol mixture obtainable in a method according to the invention is essentially free (i.e. usually 0.01 wt. % or less, preferably 0.001 wt. % or less) of glycidol, based on the total weight of the polyglycerol mixture.

Usually, the polyglycerol mixture obtainable in a method according to the invention is essentially free (i.e. usually 0.01 wt. % or less, preferably 0.001 wt. % or less) of acrolein, based on the total weight of the polyglycerol mixture.

The polyglycerol mixture obtained or obtainable in a method according to the invention may be subjected to one or more further treatments. For instance, residual glycerol may be removed or a specific polyglycerol fraction may be recovered. Suitable techniques are known in the art. Glycerol may for instance be removed by vacuum distilling or by steam stripping.

The polyglycerol (mixture) obtained or obtainable according to the invention may be used as such in a further application, e.g. in a food, cosmetic or pharmaceutical product, or it may be derivatised, first.

The derivatisation may be with any substance having reactivity with a hydroxyl group of the polyglycerol. In a preferred embodiment, the derivatisation is a reaction with an amine, a further etherification reaction, an esterification reaction or a transesterification reaction. Usually a carboxylic acid, mono-glyceride or di-glyceride is used for the esterification reaction. For transesterification a mono-, di- or triglyceride is particularly suitable, although another ester may be used as a reagent ester. Suitable carboxylic acids which may be used are C1-C30 carboxylic acids, and preferably C6-C22 carboxylic acids are used. Particularly preferred are saturated or unsaturated fatty acids, of which lauric acid, stearic acid, isostearic acid, oleic acid, palmitic acid, behenic acid, myristic acid, caprylic acid, capric acid, caproic acid, myristoleic acid, linoleic acid, oleic acid, licaneic acid, ricinoleic acid, eleostearic acid, and erucic acid are examples. The glycerides are preferably glycerides of one or more of C1-C30 carboxylic acids, in particular or one or more C6-C22 carboxylic acid.

Process conditions for esterification can be based on conditions known per se in the art for esterification with alkali bases, such as sodium hydroxide, sodium carbonate, and sodium acetate. Examples of such process conditions include those described in U.S. Pat. Nos. 5,585,506; 4,517,360; 5,006,648; 5,071,975; 5,079,355, and 3,963,699.

According to a preferred embodiment, the esterification (or transesterification) is performed by heating the polyglycerol mixture with the carboxylic acid or reagent ester (for transesterification) in the presence of the catalyst salt. The esterification is generally performed at a temperature of from about 160 to about 260° C. and preferably performed at from about 210 to about 250° C. The pressure usually is atmospheric or subatmospheric. A pressure below 1 bar is preferred for removal of water, produced in the esterification reaction.

Transesterification takes place under the same conditions with the exception that the preferred reaction temperature is 230 to 260° C.

The molar ratio of polyglycerol to carboxylic acid equivalent (or reagent ester) in the reaction mixture broadly ranges from about 1:0.5 to about 1:10. The molar ratio can be varied in order to vary the performance of the polyglycerol ester produced. Generally, the higher the molar ratio of polyglycerol to fatty acid (or triglyceride), the lower the hydrophilic-lipophilic balance (HLB) of the product.

Typically, a catalytically effective amount of the catalyst salt is present in the reaction mixture. The molar ratio of the catalyst salt to polyglycerol in the reaction mixture for the (trans)esterification generally ranges from 0.0002 to 0.2, in particular from 0.0006 to 0.02, and more preferably from about 1:0.001 to about 1:0.01.

Generally, the reaction is performed for about 1 to about 10 hours and preferably for about 2 to about 4 hours. More preferably, the reaction is continued until the reaction mixture is clear and has an Acid Value as measured by American Oil Chemists Society (A.O.C.S.) Official Method Te 1a-64 of less than 2.

After esterification, the reaction mixture can be neutralized by any method known in the art, such as with a neutralizing agent. Examples of neutralizing agents are phosphoric acid, phosphorous acid, lactic acid, acetic acid, hydrochloric acid and citric acid.

The resulting solution preferably contains less than about 8%, more preferably less than about 5%, in particular less than about 2% by weight of cyclic polyglycerol esters, based on 100% weight of total polyglycerol esters in the solution.

A polyglycerol (mixture) or a polyglycerol ester (mixture) obtained or obtainable according to the invention is in particular suitable for use in a pharmaceutical product, a cosmetic product, a textile product, a food product or a feed product. The polyglycerol or polyglycerol ester (mixture) can be formulated in a manner known per se together with one or more other (conventional) ingredients of any of said products.

The invention will now be illustrated by the following examples.

EXAMPLES

Example 1: 14 wt. % Calcium Oxide on CNF Catalyst

A 14 wt. % calcium oxide on CNF catalyst was prepared according to the method as described in Frey et al., Journal of Catalysis 2013, 305, 1-6. Typically, 5 wt. % Ni/$SiO_2$ catalyst was prepared by deposition-precipitation process at a temperature of 90° C., with nickel nitrate hexahydrate (7.85 g), silica (30 g, Aerosol 300, Degussa) and urea (4.85 g) in water (1.3 L). This material was used as a growth catalyst after calcination (T=600° C.) and reduction (T=700° C., with $H_2$). CNFs were grown from the growth catalyst (5 g) by using syngas ($H_2$/CO/$N_2$, 102/266/450 mL $min^{-1}$) at a temperature of 550° C. and a pressure of 380 kPa. The CNFs were purified by a reflux treatment in 1 M KOH for a period of 1.5 h to remove the silica and, after washing, a subsequent reflux treatment with concentrated $HNO_3$ for a period of 1.5 h to remove nickel and to functionalize the fibers. Surface oxidized CNFs (typically 30 g) were obtained after the wash.

2.5 g of surface-oxidized CNFs having an average sieve fraction of 212 to 425 μm were impregnated by incipient wetness under vacuum with a 5.3 M aqueous solution of calcium nitrate (1.5 g Ca($NO_3$)$_2$.4$H_2$O in 1.25 mL). The catalyst was equilibrated for 1 h at room temperature (about 25° C.), then dried at a temperature of 120° C. for 12 h in static air (no gas flow). The impregnated calcium nitrate was converted to calcium oxide by heat treatment of the impregnated CNFs with a temperature ramp rate of 5° C./min to 800° C. which was maintained for 3 h in a $N_2$ atmosphere. The materials were stored prior to use under an argon atmosphere to avoid exposure to $CO_2$ and $H_2O$ in the air.

Example 2: 14 wt. % CaO_AC Catalyst

A 14 wt. % CaO_AC catalyst was prepared according to the method as described above for 14 wt. % CaO_CNF (Example 1), except using activated carbon (Norit sx ultra cat) as the support and a 1.7 M calcium nitrate solution (1.5 g Ca($NO_3$)$_2$.4$H_2$O in 3.75 mL $H_2$O) for the incipient wetness impregnation, as the total pore volume of the activated carbon (Norit sx ultra cat) was larger (0.88 $cm^3$/g) than the CNF (0.5 $cm^3$/g).

Example 3: 0.37 wt. % Ca(OH)$_2$ Catalyst (Reference)

For the Ca(OH)$_2$ catalyst a commercially available conventional product was used.

Example 4: 2 wt. % Non-Supported CaO—C Catalyst (Reference)

A CaO—C catalyst was prepared as in Chem. Eur. J. 2008, 14, 2016-2024.

A solution of calcium methoxide was prepared by dissolving metallic Ca (16.8 g) in dry methanol (800 mL). The mixture was stirred for 16 h under a flow of Ar. Then the solution of Ca(OCH$_3$)$_2$ in methanol (150 mL) was stirred in a beaker with toluene (450 mL). Calcium methoxide in this mixture was immediately hydrolyzed by dropwise addition of de-ionized water (8 mL) at room temperature. The reaction mixture was then transferred into an autoclave and flushed with Ar. The autoclave was loaded with $Ar_{(g)}$ to the pressure of 12 bar and heated to 245° C. The final pressure in the autoclave was 39 bar and the temperature of 245° C. was maintained for 15 min. After synthesis, the autoclave was vented, flushed with $Ar_{(g)}$ for 10 min to remove the remaining organic solvents and allowed to cool down to room temperature. In the final step the obtained calcium hydroxide was thermally converted to CaO by performing the activation treatment under dynamic vacuum. $Ca(OH)_2$ was placed in a Schlenk tube, outgassed for 20 min and heated according to the following treatment: 25-350° C. at a rate of 0.5° C./min and maintaining the temperature of 350° C. for 1 h followed by further heating to 450° C. with a rate of 1° C./min and maintaining this temperature for 2.5 h.

Examples 5 and 6: Non-Supported NaOH Catalyst (Reference)

For the NaOH catalysts a commercially available conventional product was used. The NaOH concentration used in the etherification was 0.2 wt. % (Example 5) and 2 wt. % (Example 6), respectively.

Examples 7, 8 and 9: 10 wt. %, 4.8 wt. % and 2.5 wt. % CaO on CNF Catalysts

The 10 wt. %, 4.8 wt. % and 2.5 wt. % CaO on CNF catalysts were prepared according to the method as described for Example 1, except that the CNF supports were impregnated by incipient wetness under vacuum with different concentrations of aqueous solution of calcium nitrate corresponding to 3.6 M (1.06 g $Ca(NO_3)_2.4H_2O$ in 1.25 mL $H_2O$), 1.7 M (0.5 g $Ca(NO_3)_2.4H_2O$ in 1.25 mL $H_2O$) and 0.9 M (0.27 g $Ca(NO_3)_2.4H_2O$ in 1.25 mL $H_2O$), respectively.

Example 10: 10 wt. % $Ca(OH)_2$ on CNF Catalyst

A 10 wt. % $Ca(OH)_2$ on CNF catalyst was prepared according to the same method as described for Example 7, except that the CaO on CNF catalyst prepared was then treated with an additional step of flowing, water saturated $N_2$ over the CaO on CNF catalyst for 12 h.

Example 11: 10 wt. % $CaCO_3$ on CNF Catalyst

A 10 wt. % $Ca(OH)_2$ on CNF catalyst was prepared according to the same method as described for Example 7, except that the heat treatment of the impregnated CNFs was carried out with a temperature ramp rate of 5° C./min to 400° C. which was maintained for 3 h in a $N_2$ atmosphere.

Example 12: Non-Supported CaO Catalyst (Reference)

For the CaO catalyst a commercially available conventional product was used.

Examples 13 and 14: 14 wt. % and 5 wt. % CaO/AC Catalysts

The 14 wt. % and 5 wt. % CaO/AC catalyst were prepared according to the method as described above for Example 1, except using activated carbon (provided by Clariant, which had a BET surface area of 886 $m^2/g$ and a total pore volume of 0.62 $cm^3/g$) as the support and that the supports were impregnated by incipient wetness under vacuum with different concentrations of aqueous solution of calcium nitrate corresponding to 3.2 M (1.5 g $Ca(NO_3)_2.4H_2O$ in 2 mL $H_2O$) and 1.1 M (0.54 g $Ca(NO_3)_2.4H_2O$ in 2 mL $H_2O$), respectively.

Example 15: 5 wt. % CaO on CNF Catalyst

The 5 wt. % CaO on CNF catalyst was prepared according to the method as described for Example 1, except that the CNF support was impregnated by incipient wetness under vacuum with a different concentration of aqueous solution of calcium nitrate corresponding to 1.8 M (0.54 g $Ca(NO_3)_2.4H_2O$ in 1.25 mL $H_2O$).

Characterization of Catalysts

The catalysts according to Examples 1, 7-9, 13 and 14 were characterized by transmission electron microscopy (TEM) using a FEI Tecnai 20F. Samples of the catalysts were placed on holy carbon grids and both bright field and dark field TEM images were recorded.

Figure 1:
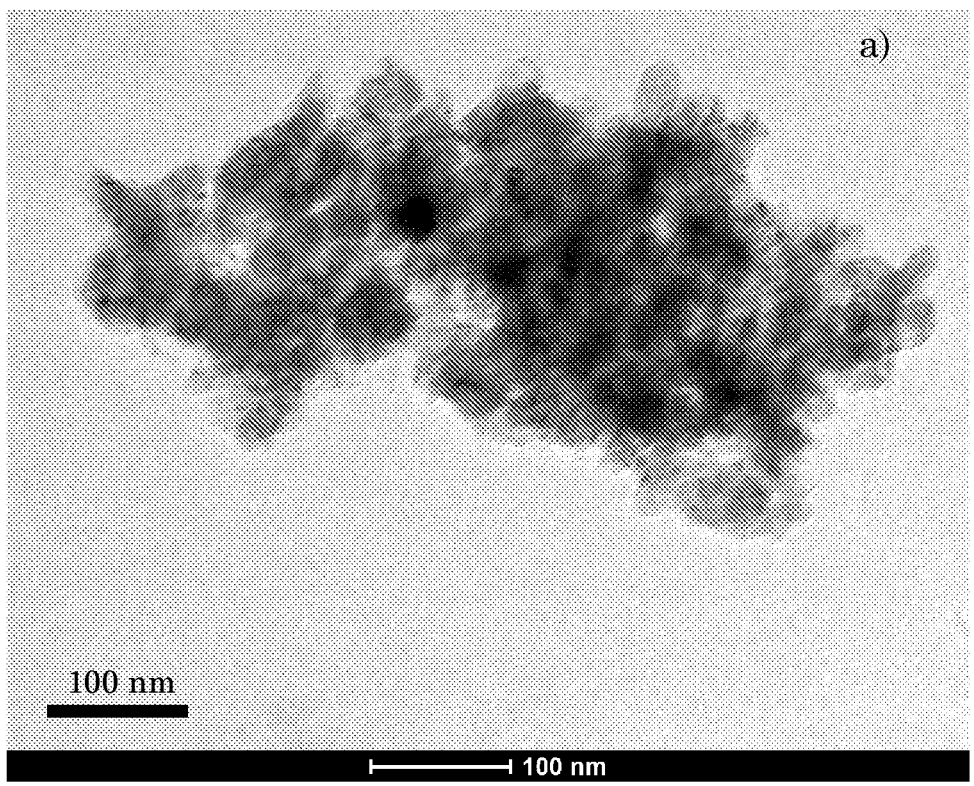
Figure 1:
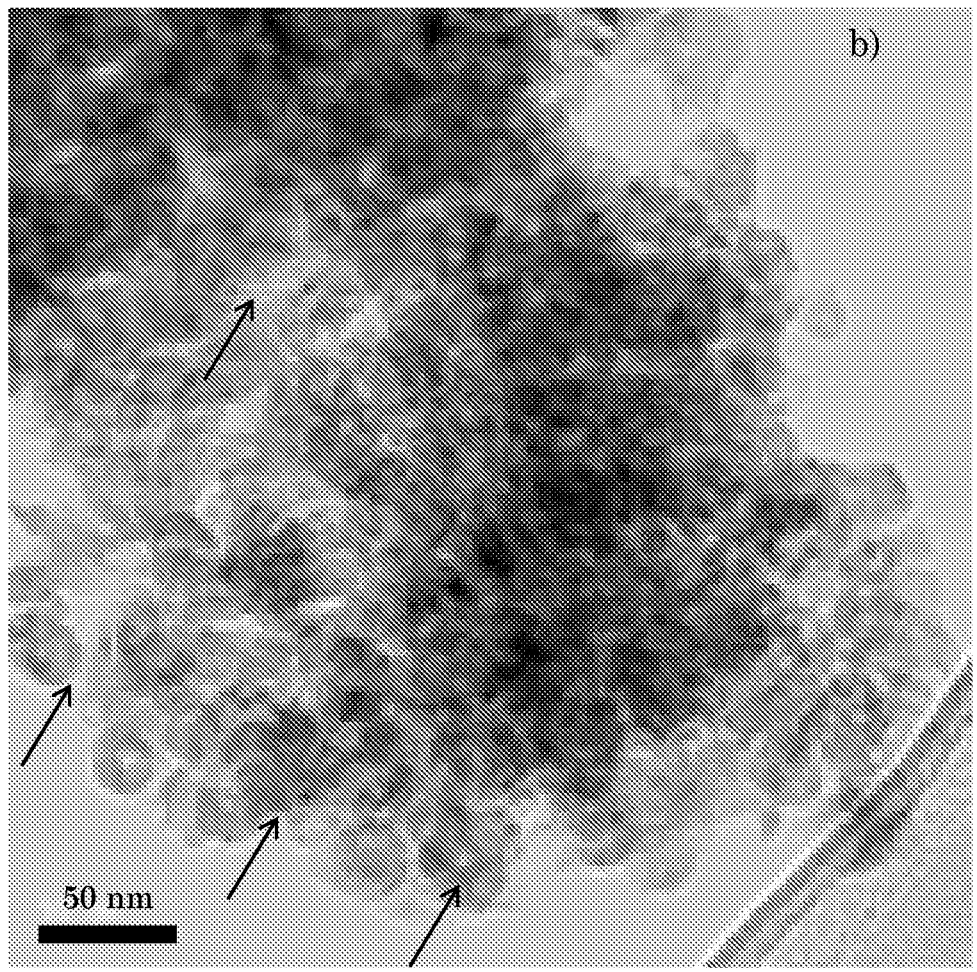
Figure 1:
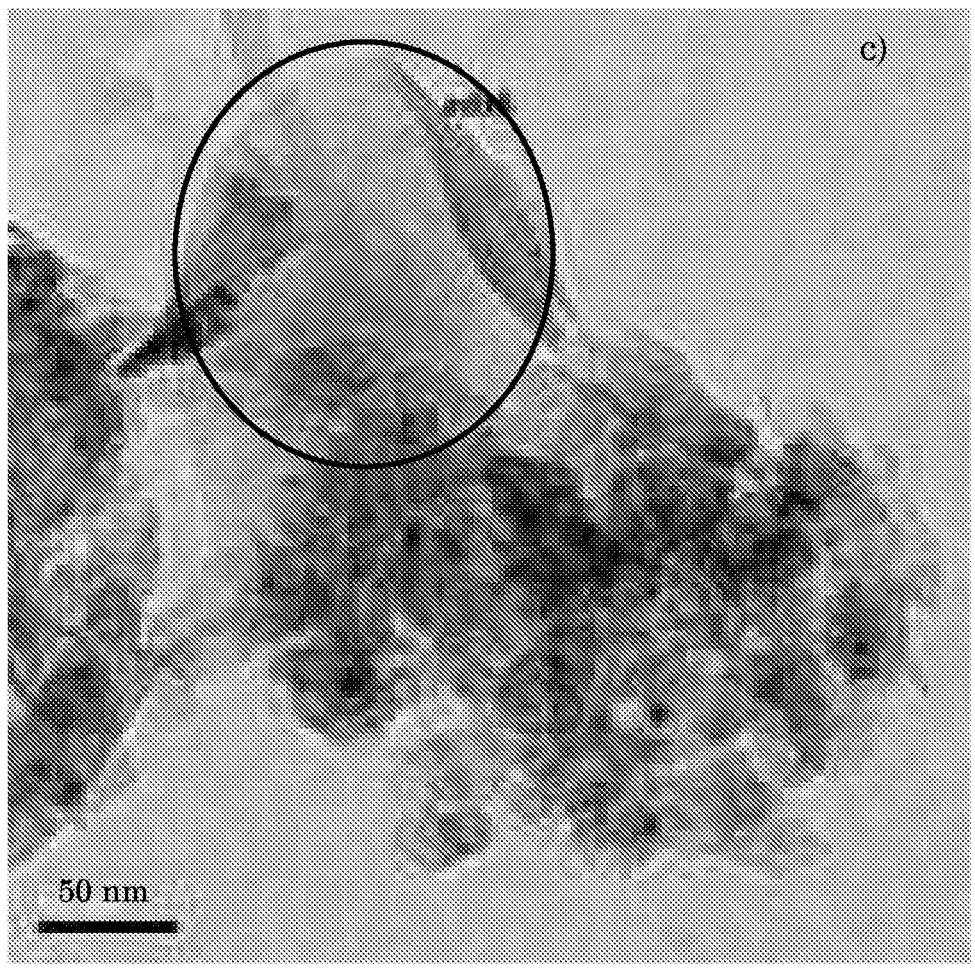

FIGS. 1 (a) and (b) show a TEM image of the catalyst of Example 9 (2.5 wt. % CaO on CNF) and Example 8 (4.8 wt. % CaO on CNF) in bright field, respectively. In these images it can be seen that the majority of the CaO on the CNF support was in the form of nanoparticles having an average size ranging of between 5-10 nm.

FIG. 1 (c) shows a TEM image of the catalyst of Example 1 (14 wt. % CaO on CNF) in bright field. In this image it can be seen that the majority of CaO is present on the CNF support in the form of a film or sheet as indicated by the circled region. Particles were not able to be observed by TEM but the Energy Dispersive X-ray detector (EDX) attached to the TEM was able to show that the CNF support was covered with CaO (see circled region in FIG. 1 (c)). The catalyst of Example 7 (10 wt. % CaO on CNF) also showed that the majority of CaO present on the CNF support in the form of a film or sheet.

The characterization of the catalysts of Examples 9, 13 and 14 by TEM showed poor contrast with the CaO being difficult to visualize.

The crystalline phases present in the catalysts according to Examples 1 and 7-12 were determined by powder X-ray diffraction (XRD) using a Bruker-AXS D2 Phaser powder X-ray diffractometer using Co $K_\alpha$ radiation ($\lambda$=1.789 Å). Measurements were carried out between 10-80 °2θ using a step size of 0.08 °2θ and a scan speed of 1 s.

Figure 2:
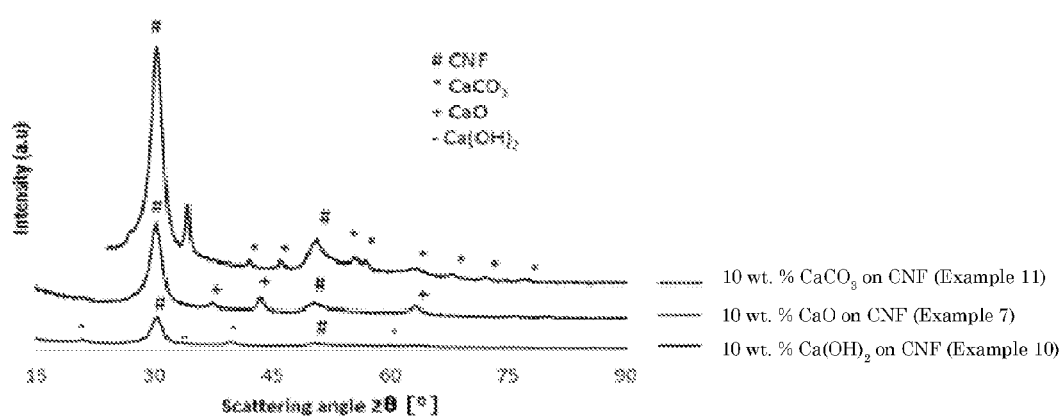

FIG. 2 shows the XRD pattern of the catalysts according to Examples 7 (10 wt. % CaO on CNF), 10 (10 wt. % $Ca(OH)_2$ on CNF) and 11 (10 wt. % $CaCO_3$ on CNF). The XRD pattern of Examples 1 (14 wt. % CaO on CNF) and 8 (4.8 wt. % CaO on CNF) were similar to that of Example 7. The XRD pattern of Example 9 (2.5 wt. % CaO on CNF) was different to that Examples 1, 7 and 8, since it was dominated by the diffraction peaks originating from the CNF support.

XRD analysis was also used to calculate the crystallite size of the catalyst salt on the support for the catalysts according to Examples 1, 7, 8, 10, 11, 13 and 14 using the Scherrer equation and the results are summarized in Table 1 below. These calculations determined that the catalyst according to Example 8 (4.8 wt. % CaO on CNF) had a crystallite size of 5-11 nm for the catalyst salt, which is in agreement with the nanoparticle size of CaO as determined by TEM. It was also found that the crystallite size increased with increasing weight loading of CaO onto CNF. However, for the catalyst of Example 9 (2.5 wt. % CaO on CNF) no CaO diffraction peaks could be observed. As expected, the bulk CaO and Ca(OH)$_2$ catalysts of (Examples 12 and 3, respectively) showed much larger crystallite sizes. The bulk CaO and Ca(OH)$_2$ catalysts had low BET surface areas, 7-15 m$^2$/g in accordance with literature (J. Catal. 2013, 305, 1-6), whereas the catalyst of Example 1 had a higher BET surface areas of 124 m$^2$/g which is about half of the surface area of the CNF support, 203 m$^2$/g. The BET surface areas and total pore volumes of the catalysts were determined according to the methods as described hereinabove.

TABLE 1

Crystallite size of supported CaO calculated by XRD, specific surface area (BET SA in m$^2$/g) and total pore volume ($V_{pore}$ in cm$^3$/g) of the CaO-based catalyst materials under study.

| Catalyst | Crystallite size XRD (nm) | BET SA (m$^2$/g) | $V_{pore}$ (cm$^3$/g) |
|---|---|---|---|
| 2.5 wt. % CaO on CNF (Example 9) | n.d. | — | — |
| 4.8 wt. % CaO on CNF (Example 8) | 5-11 | — | — |
| 10 wt. % CaO on CNF (Example 7) | 8-12 | — | — |
| 14 wt. % CaO on CNF (Example 1) | 12-20 | 124 | 0.39 |
| Bulk CaO (Example 12) | 72-122 | 7 | 0.03 |
| 10 wt. % Ca(OH)$_2$ on CNF (Example 10) | 9-10 | — | — |
| 10 wt. % CaCO$_3$ on CNF (Example 11) | 16 | — | — |
| 14 wt. % CaO/AC (Example 13) | 16 | — | — |
| 5 wt. % CaO/AC (Example 14) | 15 | — | — |
| Bulk Ca(OH)$_2$ (Example 3) | 24 | 15 | 0.06 |
| CNF | n.d. | 203 | 0.49 | n.d. means not determined.

Activity Test of the Catalysts:

The activity for glycerol etherification, one of the essential features of the catalyst salt on a support to be used in the present invention, is determined as follows:

Glycerol etherification was carried out in a stirred batch reactor using the catalysts according to Examples 1-6 and 13-15. The catalysts according to Examples 1-3, 5, and 13 had about equimolar amounts of metal, while the catalysts according to Example 4 and 6 had 7 and 10 times the amount of metal, respectively. The catalysts of Examples 14 and 15 contained 1.8 mmol CaO and thus had 2.77 times less the amount of metal of the catalyst of Examples 1-3, 5 and 13.

Glycerol (100 g, Acros Organics, 99+%) and the catalysts according to Examples 1-6 (2 g for Examples 1, 2, 4, 6, and 13-15; 0.37 g for Example 3; 0.2 g for Example 5), respectively, were stirred at a temperature of 220° C. for at least 20 h under argon flow in a five-necked 250 mL flask, equipped with a mechanical stirrer at a speed of 400 rpm, and, a Dean-Stark apparatus with a reflux condenser to collect water that was removed from the reaction mixture by the flow of gas. Typically, some amounts of glycerol also condensed in the Dean-Stark apparatus.

The catalyst of Example 1 was also tested at 200° C.

GC Analysis of Polyglycerol Product Mixture

GC analysis of the resulting polyglycerol product mixture was performed by taking liquid samples periodically and analyzed after silylation according to the method as described in Sweeley et. al. Journal of the American Chemical Society 1963, 85, 2497-2507.

Typically, weighed amounts (50-60 mg) of the product mixture were mixed with pyridine (2 mL) and n-dodecanol (5 wt. % in pyridine) as internal standard in a screw-capped vial (8 mL). After dissolution, hexamethyldisilazane (HMDS, 1.6 mL) and trimethylchlorosilane (TMCS, 0.8 mL) were added and the mixture was heated to a temperature of 70° C. for 1 h. The solution was injected into a Varian GC equipped with a VF-ms capillary column and an FID detector, in a temperature-programmed mode of a temperature ramp of 10° C. min$^{-1}$ from 60 to 260° C., held for 5 min, then another temperature ramp of 20° C. min$^{-1}$ to 300° C. and held for 5 min, according to the method as described. Calibrations were performed for glycerol and diglycerol (dimers) using commercial glycerol (Acros Organics, 99+%) and diglycerol (Solvay, >90%). For the calibrations 10, 20, 30, 40, 50, 60 mg of the standards were used to construct the calibration curve. The response factor for triglycerol (trimers) and tetraglycerol (tetramers) was calculated from polyglycerol-3 (Solvay, 43.3% triglycerol, 19% tetraglycerol) and polyglycerol-4 (Solvay, 41.2% triglycerol, 35.2% tetraglycerol) and applied to the GC data obtained. The response factor for the cyclic dimers and cyclic trimers were assumed to be the same as diglycerol and triglycerol respectively. Once the percentage of glycerol, dimers, trimers, tetramers and cyclics was calculated the missing fraction was assumed to be higher oligomers.

Figure 3:
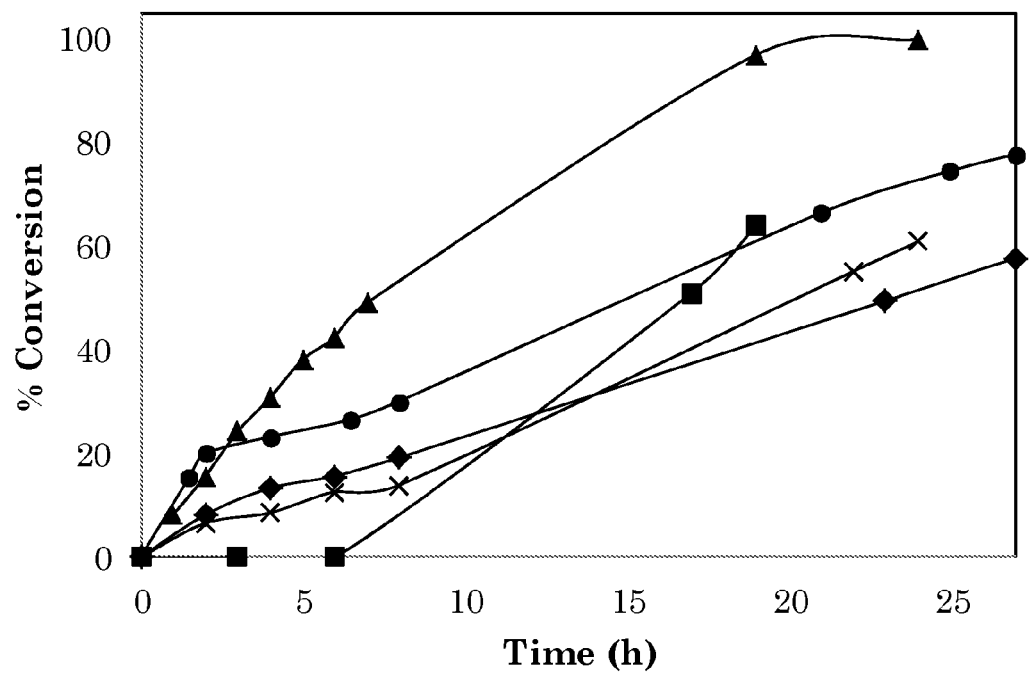
Figure 3:
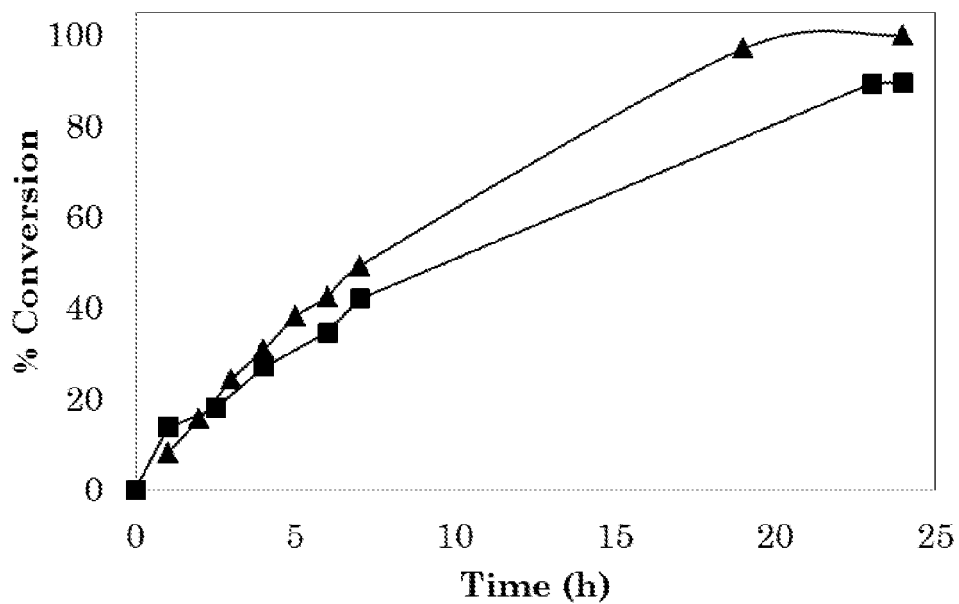
Figure 3:
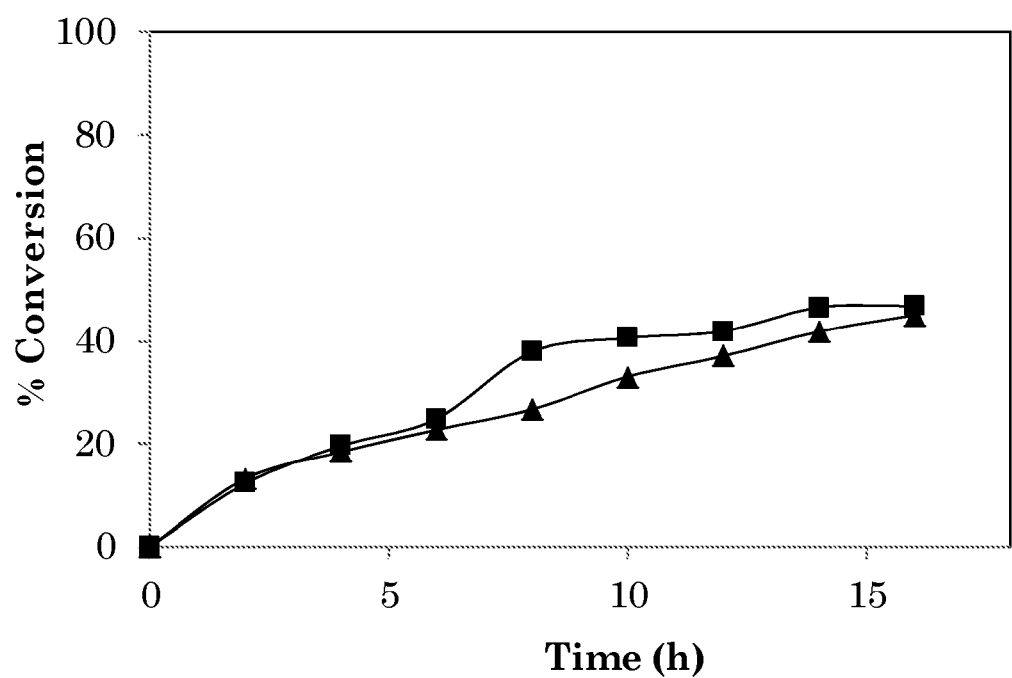

FIG. 3 (a) shows the activity of the catalysts of Example 1 (line with triangles), Example 2 (line with circles), Example 3 (line with crosses), Example 4 (line with squares) and Example 5 (line with diamonds). The catalyst of Example 1 (14 wt. % calcium oxide on CNF) had the highest activity of the catalysts tested, achieving about 50% conversion in 7 h and about 100% conversion in 24 h. The catalyst of Example 2 (14 wt. % CaO_AC) had the next highest activity, achieving 50% conversion in about 15 h.

FIG. 3 (b) shows the activity of the catalysts of Example 1 (line with filled triangles) and Example 13 (line with filled squares). The catalyst of Example 13 (14 wt. % CaO/AC) was only slightly less active than the catalyst of Example 1 (14 wt. % CaO on CNF).

FIG. 3 (c) shows the activity of the catalysts of Examples 15 (line with filled squares) and 14 (line with filled diamonds). The catalysts of Example 15 (5 wt. % CaO on CNF) and Example 14 (5 wt. % CaO/AC) were found to have a similar activity.

Figure 4:
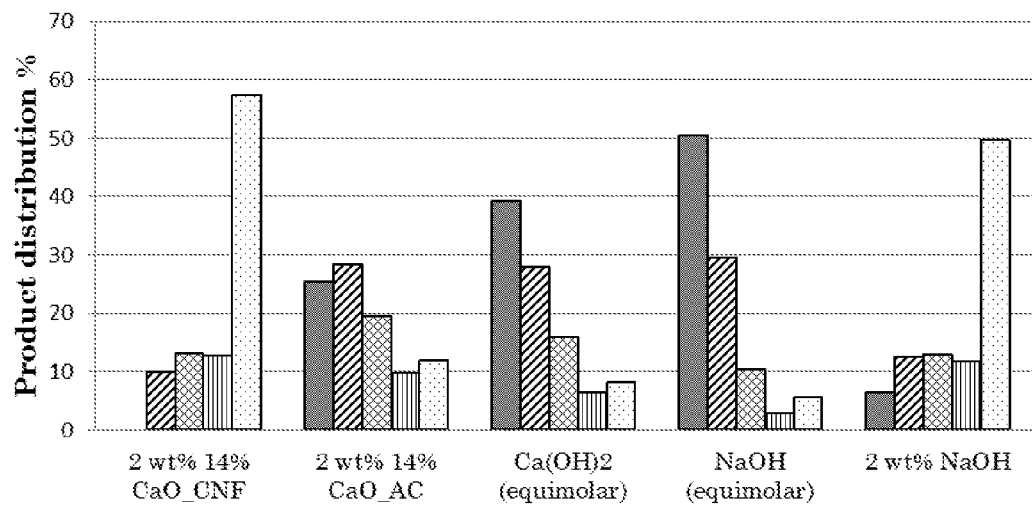

FIG. 4 shows a bar graph of the polyglycerol product distribution obtained at a reaction time of about 24 h for the catalysts of Examples 1-3, 5 and 6. The products that were measured include glycerol (fine cross hatch), diglycerol (thick diagonal lines), triglycerol (coarse cross hatch), tetraglycerol (vertical lines) and higher oligomers (dots). The 14 wt. % calcium oxide on CNF catalyst (Example 1) and the 2 wt. % NaOH catalyst (Example 6) have a similar product distribution. The 14 wt. % calcium oxide on CNF catalyst (Example 1) is also the only catalyst that does not have a polyglycerol product comprising unreacted glycerol.

Figure 5:
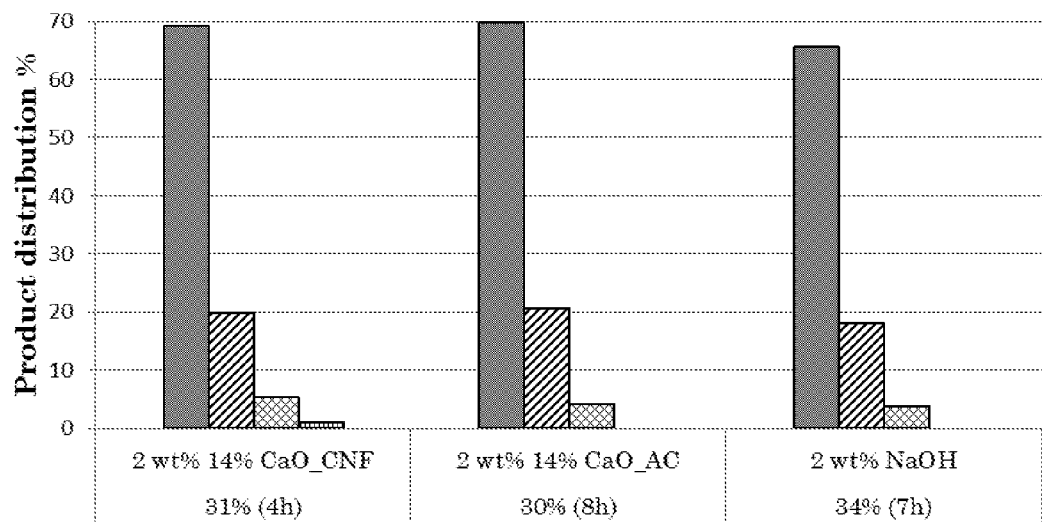
Figure 6:
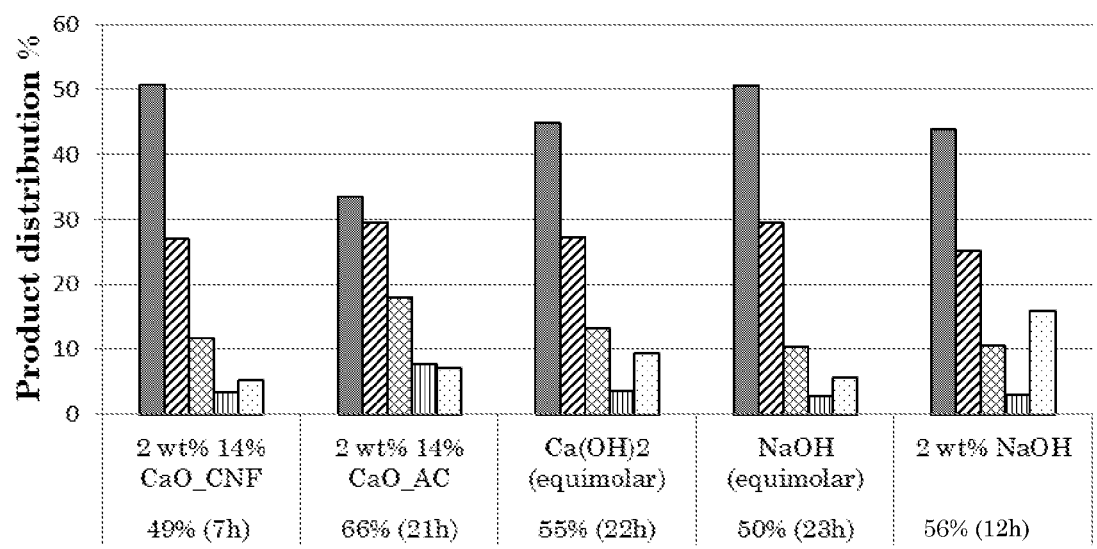

FIGS. 5 and 6 show bar graphs of the polyglycerol product distribution obtained at about 30% conversion using catalysts according to Examples 1, 2 and Example 6 and about 50% conversion using catalysts according to Examples 1-3, 5 and 6, respectively. The products that were measured include glycerol (fine cross hatch), diglycerol (thick diagonal lines), triglycerol (coarse cross hatch), tetraglycerol (vertical lines) and higher oligomers (dots). These bar graphs both show that the catalyst of Example 1 has a significantly higher activity than all the other catalysts.

Figure 7:
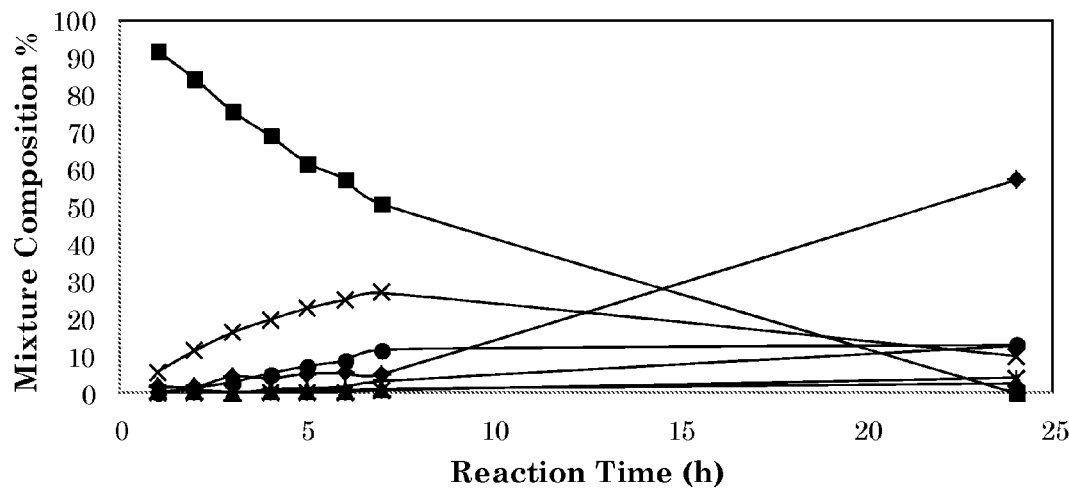
Figure 8:
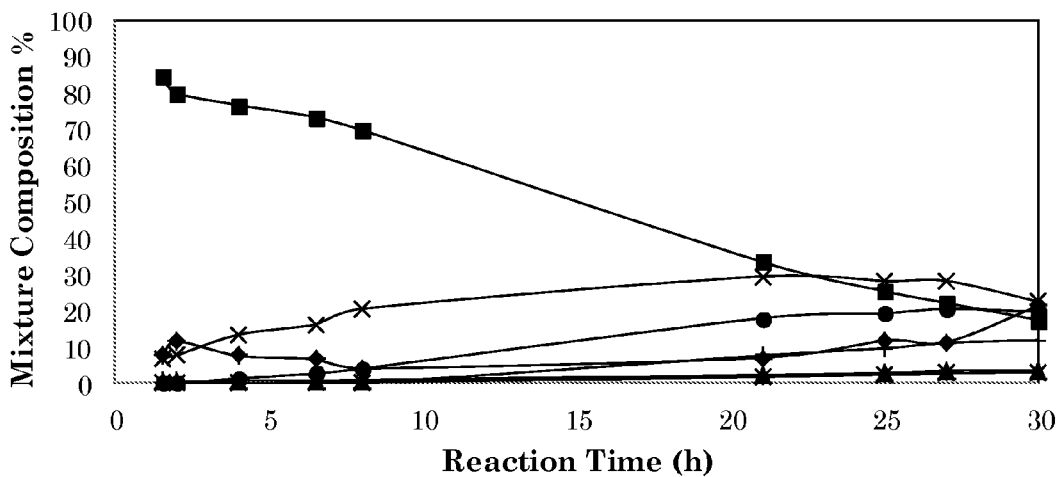
Figure 9:
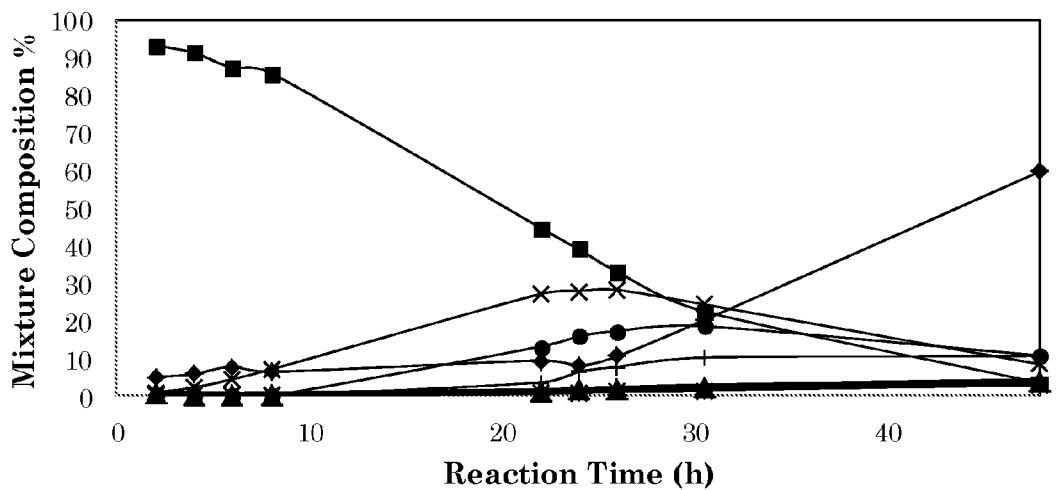
Figure 10:
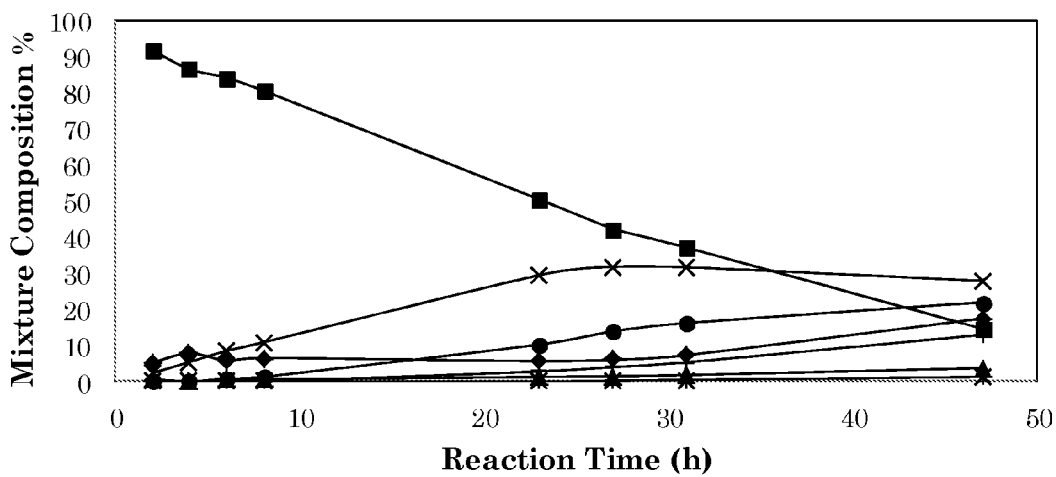
Figure 11:
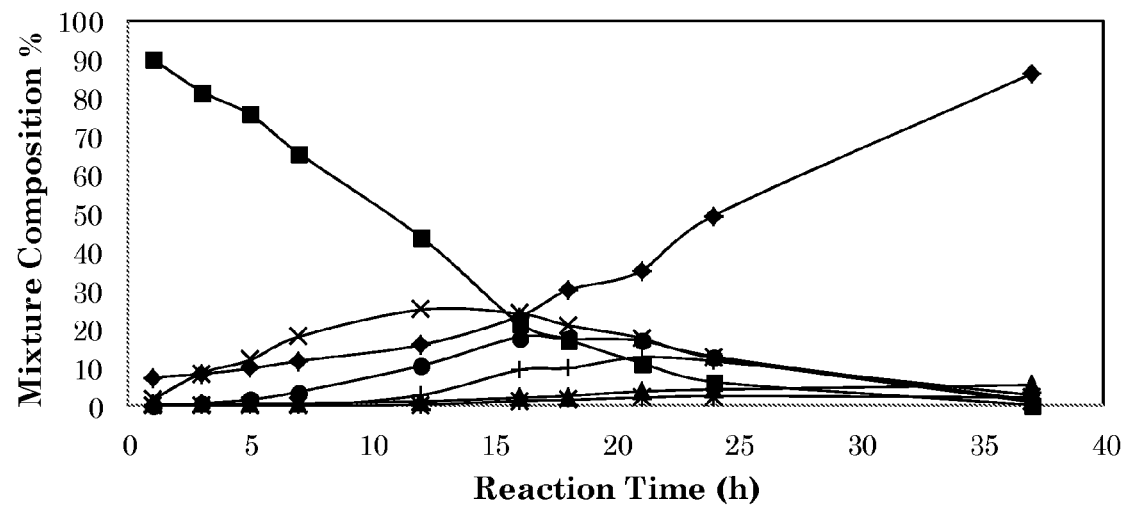
Figure 12:
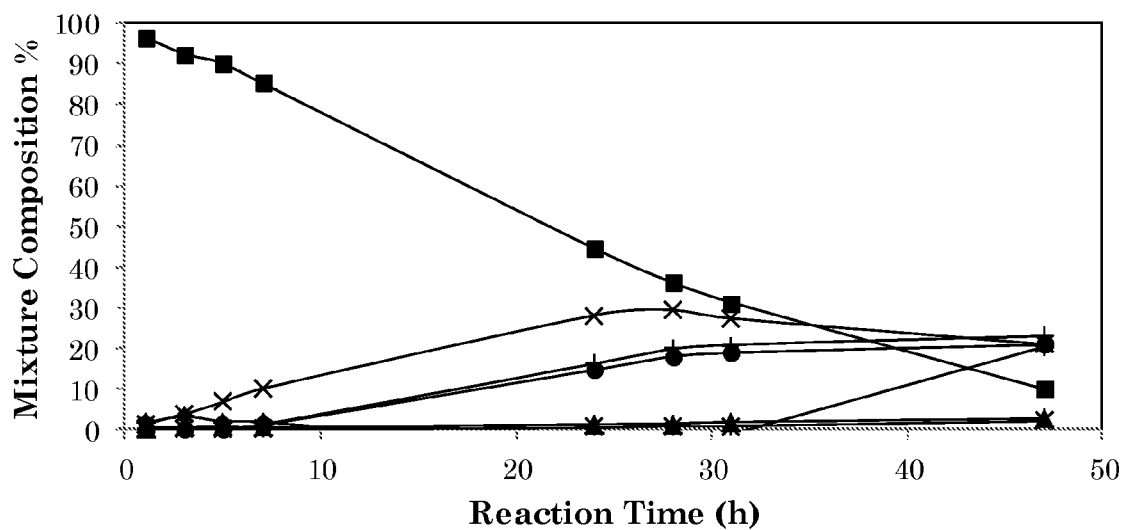

FIGS. 7-12 show the selectivity of the catalysts of Examples 1-3, 5 and 6, as well as the catalyst of Example 1 using a reaction temperature of 200° C., respectively, for converting glycerol (line with squares) to cyclic dimers (line with triangles), diglycerol (line with crosses), cyclic trimers (line with crosses having a vertical line), triglycerol (line with circle), tetraglycerol (line with vertical lines) and higher oligomers (line with diamonds). The product mixture is shown in FIGS. 7 and 12 to be influenced greatly when using a catalyst according to Example 1 (14 wt. % CaO on CNF) at different reaction temperatures (i.e. 220° C. versus 200° C.).

Additional Analysis of the Polyglycerol Product Mixtures:

The polyglycerol product mixtures obtained using catalysts of Example 1 at different temperatures (14 wt. % CaO on CNF using a temperature of 220° C. and 200° C., respectively), Example 2 (14 wt. % CaO_AC), and a commercial reference product made from NaOH (provided from Clariant) were analyzed to determine the amount of Ca in the liquid phase in parts per million (ppm) by weight of calcium after the carbon support was removed, with atomic absorption spectrometry (AAS), using a Perkin-Elmer AAS Analyst 200, hydroxyl value (HV) as determined by DIN 53240, number of glycerol units per molecule (n) (chain length for linear polyglycerol), Gardner colour number (G) as determined by DIN ISO 4630, and iodine number (J) (to determine the number of unsaturated carbon carbon bonds) and are shown in Table 2 below.

Specifically, the method used for determining the HV was as follows: 100-200 mg polyglycerol sample is placed into a 250 mL flask. 20 mL of an acetylation solution (50 ml acetic anhydride and 950 ml pyridine) is added to the sample in the flask to produce a mixture. The mixture is then dissolved by placing the flask over a steam bath. 5 mL 2 wt. % 4-dimethylaminopyridine (DMAP) in pyridine is added to the mixture in the flask, which is then stirred for 10 min at a temperature of 55° C. 15 mL H$_2$O is added to the mixture and stirred for 10 min at a temperature of 55° C. The mixture is then cooled to a temperature of 25° C. and 50 mL of 2-propanol is added. The resulting mixture is then titrated with 0.5 M NaOH. The titre of the NaOH solution is checked by titration with potassium hydrogen phthalate and using the indicator phenolphthalein (clear to red/pink at endpoint).

The HV is then calculated using the following formula:

$$HV \text{ in mg KOH/g} = [(a-b)\cdot c\cdot t\cdot M]/EW$$

wherein a is the volume of the blank sample, b is the volume of the polyglycerol sample (both in mL), c is the molar concentration of NaOH (in mmol/mL), t is the titre of the NaOH solution (dimensionless), M is the molar mass of KOH (in mg/mmol), and EW is the sample weight (in g). The titre is determinable as described in http://toolboxes-.flexiblelearning.net.au/demosites/series4/412/laboratory/methodsman/MMSOP-PrepMolSodHydSltion.htm The number of glycerol units (n) of the polyglycerol sample can be determined using the following formula:

$$n = (112200 - 18*HV)/((74.1*HV) - 56100)$$

wherein HV is the hydroxyl value.

The iodine value (J) was determined using a LICO 400 UV spectrometer, which was calibrated with a test filter set (HACH LANGE GmbH).

TABLE 2

Characteristics of polglycerol mixtures produced

| Catalyst | Reaction Time (h) | AAS (ppm) | HV (mg KOH/g) | n | G | J |
|---|---|---|---|---|---|---|
| 14 wt. % CaO on CNF (Example 1) | 1 | 1641 | — | — | — | — |
| 14 wt. % CaO on CNF (Example 1) | 20.5 | 1771 | 1037 | 4.51 | 1.3 | 1.3 |
| 14 wt. % CaO_AC (Example 2) | 30 | 2582 | 1156 | 3.09 | 3 | 2.6 |
| 14 wt. % CaO on CNF (Example 1) @ T = 200° C. | 47 | — | 882 | 10.41 | 5.8 | 8 |
| Commercial Reference product made from NaOH (provided from Clariant) | — | — | — | 7 to 10 | 7.5 | 16.6 |

Analysis of the Effect of CaO Loading on the Catalytic Activity and Selectivity

The catalysts according to Examples 7-9 (10, 4.8 and 2.5 wt. % CaO on CNF, respectively) and 35.7 mmol of the bulk catalyst of Example 12 (CaO) and 5 mmol of the bulk catalyst of Example 5 (NaOH) were tested to determine the impact of CaO loading on the etherification of glycerol.

The glycerol etherification reactions were carried out under the same conditions as described hereinabove in the Activity Test of the catalysts, except using 2 g of the catalysts of Examples 7-9 and a reaction temperature of only 220° C. A blank reaction with the CNF support material was carried out as well and this experiment revealed a conversion of 10% after 20 h. Liquid samples were taken periodically. GC analysis of the resulting polyglycerol product composition was determined according to the method as described hereinabove in the GC analysis of polyglycerol product mixture.

Figure 13:
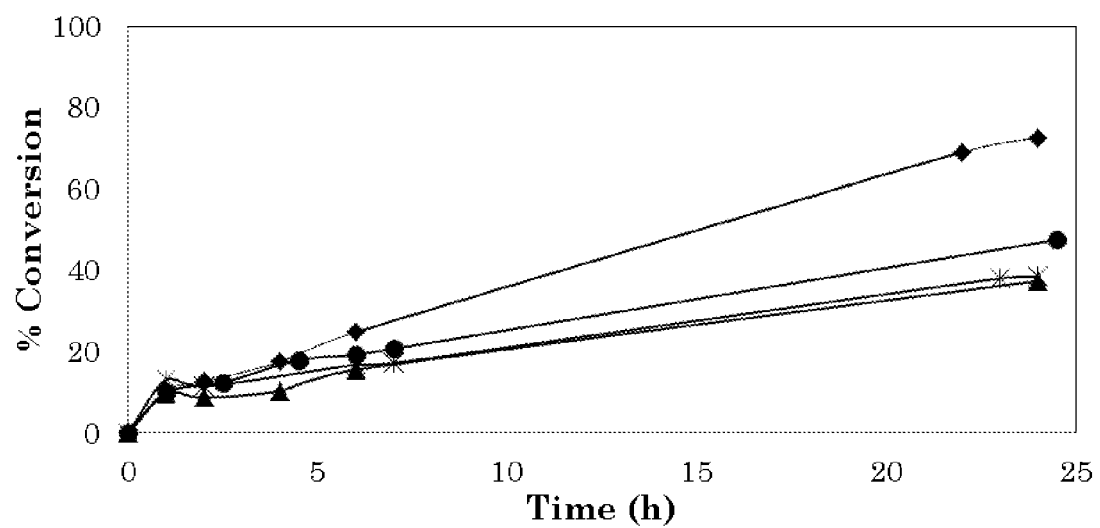

FIG. 13 shows the glycerol conversion for the catalysts of Example 7 (line with filled diamonds), Example 8 (line with filled circles), Example 9 (line with filled triangles) and 35.7 mmol of the bulk CaO catalyst of Example 12 (line with stars) as a function of time.

In FIG. 13 it can be seen that all catalyst materials are active and that the glycerol conversion increases gradually as the loading of CaO on the CNF support increases. In comparison to the previous results by Ruppert et al. in Chemistry 2008, 14, 2016-2024, no induction period was observed for the catalyst of Examples 7-9, indicating that the CaO colloids were released from the CNF support prior to the onset of the catalysis. Further, even though the bulk catalyst of Example 12 has almost 10 times more CaO compared to the catalyst of Example 7, it was a much less active catalyst. It has been found that dispersing CaO on a support material as nanoparticles and/or film greatly increases the CaO surface area which in turn increases the availability of CaO in glycerol, leading to a higher glycerol conversion.

The results of the catalytic conversion of glycerol with different catalytic materials are summarized in Table 3 below. Table 3 compares the mmol of glycerol converted per mmol of calcium used per reaction after a period of 24 h, % conversion of glycerol, and the turnover number (TON), which is the number of mmol of glycerol converted per mmol of metal after 24 h. The catalyst of Example 9 (2.5 wt. % CaO on CNF) showed the highest turnover number (TON), with TONs gradually dropping with increased Ca loading, showing that less CaO is available at higher loadings. The bulk catalyst of Example 5 (NaOH) was also evaluated as a reference catalyst. 5 mmol of NaOH had a lower glycerol etherification activity when compared to the catalyst of Example 1 (14 wt. % CaO on CNF), which had equimolar amounts of metal, reaching 50% and 100% glycerol conversion after 24 h, respectively (see Table 3).

TABLE 3

Catalytic conversion of glycerol over CaO and differently prepared catalyst materials, as well as a reference NaOH catalysts.

| Catalyst | Ca or Na loading (mmol) | % Conversion (24 h) | Glycerol converted[a] (mmol) | TON[b] |
|---|---|---|---|---|
| 2.5 wt. % Ca on CNF (Example 9) | 0.9 | 37 | 402 | 447 |
| 4.8 wt. % CaO on CNF (Example 8) | 1.7 | 48 | 522 | 307 |
| 5 wt. % CaO on CNF (Example 14) | 1.8 | 47[c] | 511 | 284 |
| 10 wt. % CaO on CNF (Example 7) | 3.6 | 72 | 783 | 218 |
| 14 wt. % CaO on CNF (Example 1) | 5.0 | 100 | 1087 | 217 |
| 5 wt. % CaO on AC (Example 15) | 1.8 | 45[c] | 489 | 272 |
| 14 wt. % CaO on AC (Example 2) | 5.0 | 75 | 815 | 163 |
| 14 wt. % CaO on AC (Example 13) | 5.0 | 90 | 978 | 196 |
| 10 wt. % Ca(OH)$_2$ on CNF (Example 10) | 3.6 | 50 | 544 | 151 |
| 10 wt. % CaCO$_3$ on CNF (Example 11) | 3.6 | 56 | 609 | 169 |
| CaO—C (Example 4) | 35.7 | 64[d] | 696 | 19 |
| CaO (Example 12) | 35.7 | 39 | 424 | 12 |
| CaO (Example 12) | 5.0 | 43 | 467 | 93 |
| NaOH (Example 5) | 5.0 | 50 | 543 | 109 |
| NaOH (Example 6) | 50.0 | 94 | 1022 | 20 |
| Ca(OH)$_2$ (Example 3) | 1.7 | 43 | 467 | 275 |
| Ca(OH)$_2$ (Example 3) | 5.0 | 49 | 533 | 107 |

[a]mmols of glycerol converted per reaction after 24 h.
[b]mmol of glycerol converted per mmol metal after 24 h.
[c]mmols of glycerol converted per reaction after 16 h.
[d]mmols of glycerol converted per reaction after 19 h.

Test reactions were preformed comparing different loadings of equimolar amounts Ca, from bulk catalysts CaO or Ca(OH)$_2$ with CaO/CNF catalysts. Differences in glycerol etherification activity were observed at different Ca loadings. At low loadings of 1.7 mmol Ca (0.16 mol. %), the calcium species dispensed by the catalyst of Example 8 (4.8 wt. % CaO on CNF) have a similar activity compared to that of the bulk 1.7 mmol catalyst of Example 3 (Ca(OH)$_2$), after 24 h, with 48% and 43% conversion, respectively. When a higher loading of 5 mmol Ca (0.46 mol. %) is used, Ca from the catalyst of Example 1 (14 wt. % CaO on CNF) produced higher activity than 5 mmol Ca from the bulk catalyst of Example 12 (CaO) or Example 3 (Ca(OH)$_2$) (see Table 3). The use of 5 mmol and 35.7 mmol of bulk CaO produced similar activities, 43% and 39% conversion respectively after 24 h (see Table 3). In the reaction with 35.7 mmol CaO, solid material was still present after 24 h and a calcium glyceroxide phase was observed in the recovered solid.

These results indicate that the solubility of (bulk) CaO plays a major role. Indeed, as CaO has a limited solubility in glycerol, at loadings up to 5 mmol all of the CaO can dissolve in the reaction mixture. It is assumed that at a Ca loading of 1.7 mmol the reaction is dominated by a homogeneous reaction pathway which is limited by solubility. Whereas, at higher loadings of e.g. 5 mmol Ca there is also a contribution from a heterogeneous reaction pathway, due to the presence of colloidal CaO/Ca(OH)$_2$ particles. Previous studies by Ruppert et al. in Chemistry 2008, 14, 2016-2024, with 35.7 mmol CaO describe that after an induction period, Ca(OH)$_2$ colloids were produced which have high catalytic activity. By dispersing CaO on a CNF support, colloidal nanoparticles can be efficiently dispensed without an induction period, which produces higher activities than equimolar amounts of bulk CaO in glycerol etherification.

Figure 14:
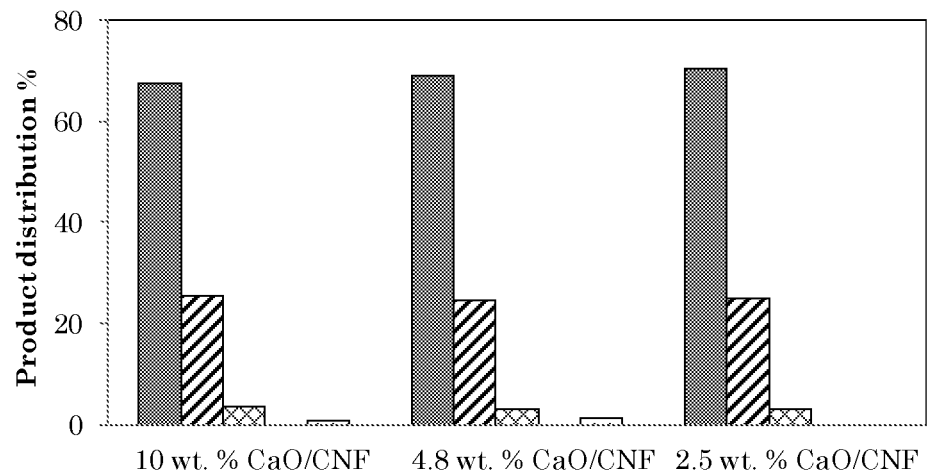
Figure 15:
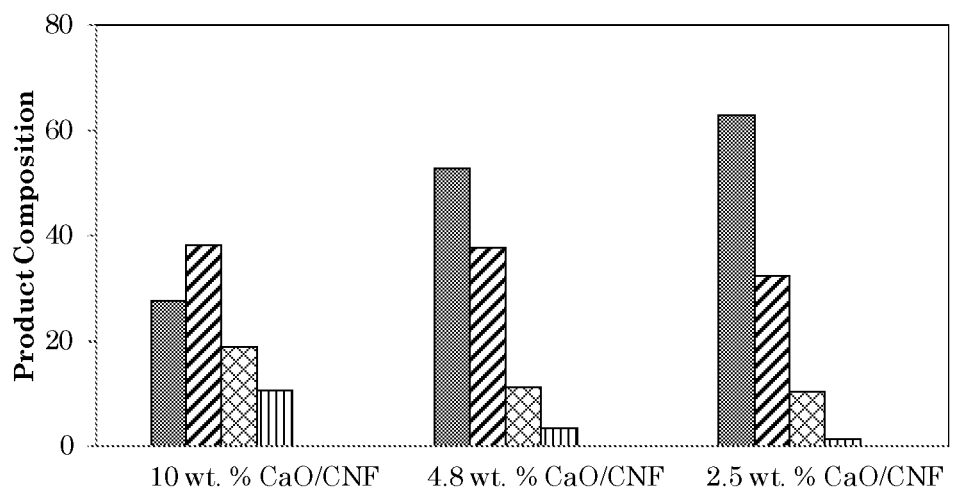

FIGS. 14 and 15 show a bar graph of the polyglycerol product distribution obtained for the CaO on CNF catalysts of different weight loadings (Examples 7-9, respectively) at 30% conversion and after 24 h, respectively. The different polyglycerol products obtained are indicated in FIGS. 14 and 15 as follows: glycerol (fine cross hatch), dimers (thick diagonal), trimers (coarse cross), tetramers (vertical lines) and higher oligomers (dots).

FIG. 14 also shows that the polyglycerol product distribution obtained at 30% conversion are all very similar for the different catalysts. However, after 24 h of reaction time, significant differences in polyglycerol product distributions were seen in FIG. 15. The catalyst of Example 7 (10 wt. % CaO on CNF) showed the highest percentage of lower oligomers, i.e. dimers and trimers (57 wt. %, based on the total weight of polyglycerols).

The efficiency of the release of the colloidal CaO into the reaction mixture from the CNF was determined using a catalyst of Example 1 (14 wt. % CaO on CNF) and by performing a hot filtration of the reaction mixture to remove the CNF half way through the reaction.

Figure 16:
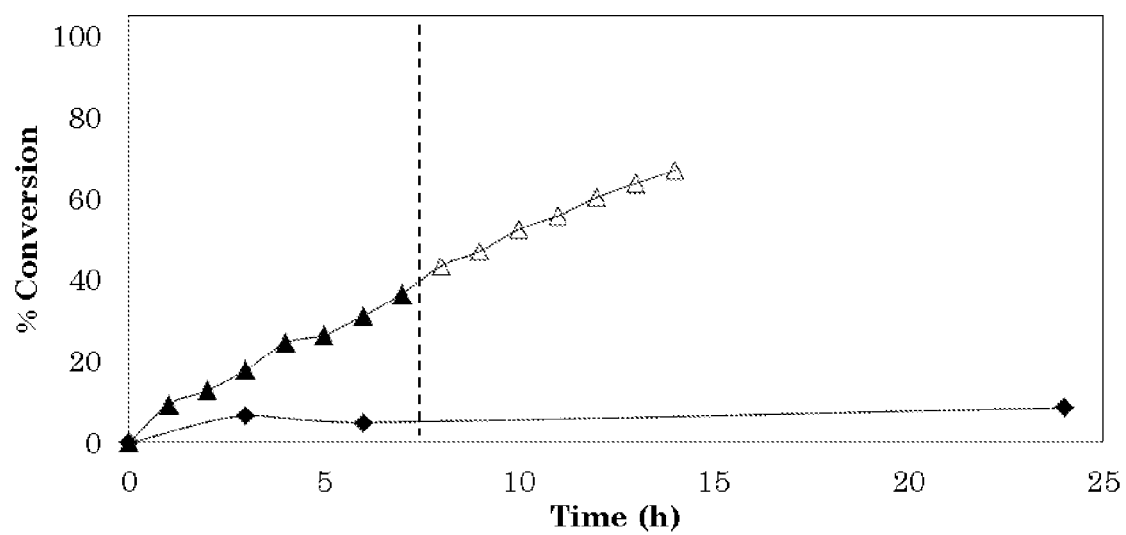
FIG. 16 shows the results of the efficiency of the % conversion vs time (h) in the etherification of glycerol by the release of colloidal CaO using a catalyst of Example 1 (line with filled triangles), a spent catalyst of Example 1 (line with filled diamonds), and the conversion after the removal of the CNF by hot filtration (open triangles).

FIG. 16 shows the results of the efficiency of the % conversion vs time (h) in the etherification of glycerol by the release of colloidal CaO using a catalyst of Example 1 (line with filled triangles), a spent catalyst of Example 1 (line with filled diamonds), and the conversion after the removal of the CNF by hot filtration (line with open triangles). A spent catalyst is defined herein as a catalyst of Example 1 which had been used in an etherification reaction of glycerol, then isolated and reused in another etherification reaction of glycerol. The data shown in FIG. 16 shows that the etherification reaction continued at the same high rate, while the recovered CNF did not give any significant activity upon reuse. This confirmed that all the CaO has been dispensed into the reaction mixture. A Perkin-Elmer AAS analysis confirmed that 83 wt. % of Ca from the original CaO/CNF material can be found in the liquid phase already after 1 h of reaction. XRD analysis of the removed carbon material showed only CNF diffraction.

Analysis of the Influence of the Ca Phase

The sensitivity of CaO to $CO_2$ and $H_2O$ and the phase behavior and reactivity of CaO was studied by comparing catalysts of Example 10 (10 wt. % $Ca(OH)_2$ on CNF) and Example 11 (10 wt. % $CaCO_3$ on CNF) with the catalyst of Example 7 (10 wt. % CaO on CNF) in the etherification of glycerol.

The glycerol etherification reactions were carried out under the same conditions as described hereinabove in the Activity Test of the catalysts, except using 2 wt. % of the catalysts of Examples 7, 10 and 11, each catalyst containing 3.6 mmol of $Ca^{2+}$, and a reaction temperature of only 220° C.

Figure 17:
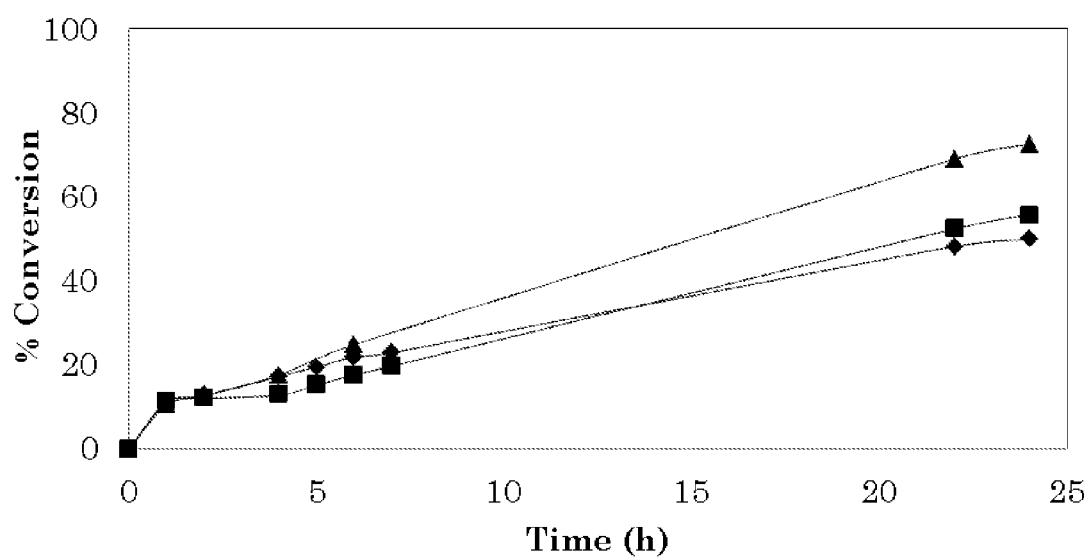
FIG. 17 shows the effect of the calcium salt on glycerol conversion after 24 h reaction time using catalysts of Example 7 (line with filled triangles), Example 11 (line with filled squares) and Example 10 (line with filled diamonds).

FIG. 17 shows the effect of the calcium salt on glycerol conversion after 24 h reaction time for the catalysts of Example 7 (line with filled triangles), Example 11 (line with filled squares) and Example 10 (line with filled diamonds). FIG. 17 also shows that catalyst of Example 7 (10 wt. % CaO on CNF) is the most active catalyst, with 73% conversion after 24 h. There was no difference observed in the selectivity between the catalysts.

Analysis of CaO Stability and Related Colloidal Particle Formation

Light scattering techniques were used to characterize the Ca colloids present for the calcium based catalysts. Static light scattering (SLS) was performed with a FICA 50 setup at a wavelength $\lambda_0$=546 nm and a temperature of 25° C. The samples were diluted with water in order to decrease the viscosity. During preparation the mixtures were not protected from dust so the samples were filtered prior to the measurements. Milliporous FP 0.8 μm filters were used. The scattered light intensity was measured as a function of the scattering angle (from 20 to 140) according to the method as described by Sacana et. al. in Langmuir 2006, 22, 10209-10216.

Samples were taken after 24 h, from glycerol etherification test reactions carried out under the same conditions as described hereinabove above in the Activity Test of the catalysts, except that the catalysts used were Example 1 (14 wt. % CaO on CNF), Example 8 (4.8 wt. % CaO on CNF) and Example 3 ($Ca(OH)_2$), at two Ca loadings of 5 mmol and 1.7 mmol and the reaction temperature used was only 220° C.

FIG. 18 shows the results of the SLS measurements in a graph plotting the scattered light intensity (a.u.) vs. the scattering angle ($K^2[m^{-2}]$) for the catalysts of Example 1 (black dotted line) and Example 8 (black dashed line), their equivalent Ca molar amounts of 5 mmol and 1.7 mmol of the catalyst of Example 3 (light grey and dark grey, respectively) and glycerol (black).

In the case of 5 mmol Ca, the scattering intensity of the Ca colloids originating from the catalyst of Example 3 ($Ca(OH)_2$), was more intense, suggesting the formation of a higher number of small particles or a lower number of larger particles from 5 mmol of the catalyst of Example 3 (Ca $(OH)_2$), than from the catalyst of Example 1 (14 wt. % CaO on CNF). The generation of a smaller number of larger colloids from 5 mmol $Ca(OH)_2$ could explain the higher activity observed for the catalyst of Example 1 (14 wt. % CaO on CNF) compared to 5 mmol of the catalyst of Example 3 ($Ca(OH)_2$) (see Table 3). There was no significant difference in the scattering intensity produced from the colloids of the catalyst of Example 8 (4.8 wt. % CaO on CNF) and 1.7 mmol of the catalyst of Example 3 ($Ca(OH)_2$). This correlates well with the similar glycerol conversions produced by these two catalysts (see Table 3) and confirms that colloids do not play a major role in the etherification reaction at this Ca loading.

Dynamic light scattering (DLS) was performed by a Malvern Zetasizer Nano using the same samples as for SLS. The derived count rate (DCR), a measure of dynamic light scattering (DLS) intensity in kilo counts per second, showed the same trend as that seen in SLS. The colloids generated from the catalysts of Example 3 ($Ca(OH)_2$) have a higher intensity compared to the colloids generated from the catalysts of Example 1 (14 wt. % CaO on CNF) and Example 8 (4.8 wt. % CaO on CNF). High polydispersity indices (PDIs) of 0.9 and 0.7 were found for the colloidal particles produced from catalysts of Examples 1 and 8, respectively, while the 1.7 mmol and 5 mmol samples of the catalyst of Example 3 gave a PDI of 1. As PDI values greater than 0.7 indicate that the sample has a very broad size distribution, this precluded further quantification of the particle size.

Conductivity measurements were employed to provide further insight into the relative contribution of molecular/homogeneous $Ca^{2+}$ species during glycerol etherification (see Table 4 and FIG. 19). The conductivity was measured using a Seven Excellence Conductivity Meter with a conductivity probe Inlab 731. The samples were diluted with water in order to decrease the viscosity.

Samples were taken after 24 h from glycerol etherification test reactions carried out under the same conditions as described hereinabove in the Activity Test of the catalysts, except using 2 wt. % of the catalysts of Example 1 (14 wt. % CaO on CNF), Example 7 (10 wt. % CaO on CNF), Example 8 (4.8 wt. % CaO on CNF), Example 9 (2.5 wt. % CaO on CNF); 1.7 mmol and 5 mmol of the catalyst of Example 3 ($Ca(OH)_2$); and, 5 mmol and 35.7 mmol of the catalyst of Example 12 (CaO) and a reaction temperature of only 220° C.

FIG. 19 shows the conductivity (K) of the polyglycerol product mixtures obtained using 2 wt. % of the catalysts of Examples 1 and 7-9 (line with filled squares); and 1.7 mmol and 5 mmol of the catalyst of Example 3 (line with filled triangles) after 24 h reaction time. FIG. 19 also shows that the conductivity increases upon increasing the amount of Ca in the reaction. Similar conductivities were observed with 1.7 mmol of Ca from the catalysts of Example 8 (4.8 wt. % CaO on CNF) and Example 3 ($Ca(OH)_2$), 184 and 197 μS/cm respectively (see Table 4). As these catalyst produce similar activities it could be assumed that mainly homogeneous catalysis occurred at this Ca loading.

TABLE 4

Derived count rates (a.u.) from dynamic light scattering measurements and conductivity (μS/cm) of product mixtures at various Ca loadings after 24 h reaction time.

| Catalyst | mmol Ca | DCR (a.u.) | Conductivity (μS/cm) |
|---|---|---|---|
| 2.5 wt. % CaO on CNF (Example 9) | 0.9 | n.d. | 124 |
| 4.8 wt. % CaO on CNF (Example 8) | 1.7 | 3.9 | 184 |
| 10 wt. % CaO on CNF (Example 7) | 3.6 | n.d. | 337 |
| 14 wt. % CaO on CNF (Example 1) | 5.0 | 5.2 | 423 |

TABLE 4-continued

Derived count rates (a.u.) from dynamic light scattering measurements and conductivity (μS/cm) of product mixtures at various Ca loadings after 24 h reaction time.

| Catalyst | mmol Ca | DCR (a.u.) | Conductivity (μS/cm) |
|---|---|---|---|
| Ca(OH)$_2$ (Example 3) | 1.7 | 2.6 | 197 |
| Ca(OH)$_2$ (Example 3) | 5.0 | 8.5 | 699 |
| CaO (Example 12) | 5.0 | n.d. | 485 |
| CaO (Example 12) | 35.7 | n.d. | 1059 | n.d. means not determined.

Comparing the catalysts of Example 1 (14 wt. % CaO on CNF) and 5 mmol of Example 3 (Ca(OH)$_2$) or Example 12 (CaO), no remaining solid CaO was observed in the product polyglycerol mixture after reaction in both cases and higher conductivities were recorded for the bulk catalysts of Example 3 and 12 (Ca(OH)$_2$ and CaO, respectively). There was a lower amount of dissolved Ca$^{2+}$ present with the catalyst of Example 1 (14 wt. % CaO on CNF), which indicated the increase in activity was not due to an increase in Ca$^{2+}$ in the reaction mixture. At this CaO loading the amount of Ca$^{2+}$ that is soluble in the reaction mixture has reached its limit and it was assumed that the rest of the Ca was present in a colloidal form. From the SLS results shown in FIG. 18, it can be seen that the catalyst of Example 1 (14 wt. % CaO on CNF) scatters light with a lower intensity. Therefore, the activity difference between the catalyst of Example 1 (14 wt. % CaO on CNF) and 5 mmol of the bulk catalysts of Examples 3 or 12 (Ca(OH)$_2$ or CaO, respectively) could be explained by smaller Ca colloids being produced from the catalyst of Example 1 (14 wt. % CaO on CNF) which gave a higher total surface area of CaO and hence, more active sites.

Analysis of the Effect of Temperature on Activity and Product Colouration

The effect of temperature on the activity and polyglycerol mixture product colouration was determined by carrying out glycerol etherification test reactions under the same conditions as described hereinabove above, except using the catalyst of Example 7 (10 wt. % CaO on CNF) and reaction temperatures of 180, 200, 220, 240 and 260° C.

FIG. 20 shows the effect of reaction temperature on glycerol conversion in a graph plotting % glycerol conversion vs time (h), with the catalyst of Example 7 (10 wt. % CaO on CNF) at reaction temperatures of 180° C. (line with x's), 200° C. (line filled triangles), 220° C. (line with filled diamonds), 240° C. (line with +'s) and 260° C. (line with filled circles).

Lower reaction temperatures of 180-200° C., produced a lower conversion of glycerol (see FIG. 20). On increasing the reaction temperature (220, 240, 260° C.) the glycerol conversion increased progressively with increasing temperature. After 24 h of reaction time at 220° C. the polyglycerol mixture product was colourless. At 240° C. there was a slight discolouration of the polyglycerol product mixture after 16 h. However, at 260° C. acrolein and condensation products were observed, which darkened the polyglycerol mixture product. Discoloration of the polyglycerol mixture product could be observed after only 2 h. At 220° C., reaction times greater than 24 h produced polyglycerol mixtures with a longer oligomer chain length but the colouration also increased with reaction time. In the case of the catalyst of Example 1 (14 wt. % CaO on CNF), if the reaction was allowed continue to 100% glycerol conversion the polyglycerol product mixture had a slight colour, Gardner colour number 1.3, and an average chain length of n was 4.5 glycerol units per molecule, determined from hydroxyl value analysis. The Gardner colour number and average chain length of n, were determined by the methods as described hereinabove.

The invention claimed is:

1. A method for preparing polyglycerol, comprising:
providing a catalyst salt on a support, the catalyst salt having catalytic activity with respect to an etherification reaction of a polyol selected from the group of glycerol and oligoglycerols, and wherein the support is a release material, which when brought into contact with the fluid phase, releases the catalyst salt in the form of colloidal particles into the fluid phase;
contacting the catalyst salt on the support with a fluid phase comprising a polyol selected from the group of glycerol and oligoglycerols; and
subjecting the polyol in the fluid phase to an etherification reaction in the presence of the catalyst salt, thereby forming the polyglycerol.

2. The method according to claim 1, wherein the fluid phase is heated to a temperature of 180-260° C. and the colloidal particles of the catalyst salt are released from the support upon heating.

3. The method according to claim 1, wherein the support is a carbon nanofiber.

4. The method according to claim 1, wherein the support is activated carbon.

5. The method according to claim 1, wherein the catalyst salt is a salt selected from the group of alkaline earth metal salts and alkali metal salts.

6. A polyglycerol mixture having a hydroxyl value in the range of 846-1072 mg KOH/g, as determined by DIN 53240; and a Gardner colour number, as determined by DIN ISO 4630, of 2 or less; and wherein the polyglycerol mixture consists of at least 85 wt. % polyglycerols.

7. The polyglycerol mixture according to claim 6, wherein the polyglycerol mixture comprises at least 30 wt. % linear polyglycerols, based on total polyglycerols.

8. The polyglycerol mixture according to claim 6, which is essentially free of acrolein and essentially free of glycidol.

9. The polyglycerol mixture according to claim 6 wherein the calcium content is 0-2000 ppm by weight.

10. A method for preparing a polyglycerol derivative, comprising reacting a polyglycerol mixture according to claim 6 with a substance having reactivity with a hydroxyl group of the polyglycerol.

11. A polyglycerol derivative obtainable by a method according to claim 10, wherein the reaction is an esterification reaction with a carboxylic acid or a transesterification with another ester.

12. A pharmaceutical product, a cosmetic product, a textile product, a food product or a feed product, comprising a polyglycerol mixture according to claim 6 and one or more other ingredients for any of said products.

13. A method for preparing a pharmaceutical product, a cosmetic product, a textile product, a food product or a feed product, comprising combining a polyglycerol mixture according to claim 6 with one or more other ingredients for any of said products.

14. A catalyst salt on a support, the catalyst salt having catalytic activity with respect to an etherification reaction of a polyol selected from the group of glycerol and oligoglycerols, wherein the support comprises 1-15 wt. % catalyst salt, based on the total weight of the catalyst salt and support, wherein the salt is a calcium salt and the support is a carbon support material, which carbon support material is selected from the group consisting of carbon nanofibers and activated carbon.

15. The catalyst salt on a support according to claim 14, wherein the calcium salt is a calcium oxide.

16. The catalyst salt on a support according to claim 14, wherein the carbon support material is a carbon nanofiber.

17. A method for preparing polyglycerol, comprising:
providing a catalyst salt on a support, the catalyst salt having catalytic activity with respect to an etherification reaction of a polyol selected from the group of glycerol and oligoglycerols, and wherein the support comprises 1-15 wt. % catalyst salt, based on the total weight of the catalyst salt and support;
contacting the catalyst salt on the support with a fluid phase comprising a polyol selected from the group of glycerol and oligoglycerols; and
subjecting the polyol in the fluid phase to an etherification reaction in the presence of the catalyst salt, thereby forming the polyglycerol.

* * * * *